United States Patent
Webler et al.

(10) Patent No.: US 7,981,152 B1
(45) Date of Patent: Jul. 19, 2011

(54) VASCULAR DELIVERY SYSTEM FOR ACCESSING AND DELIVERING DEVICES INTO CORONARY SINUS AND OTHER VASCULAR SITES

(75) Inventors: William E. Webler, Escondido, CA (US); Neil Becker, Fallbrook, CA (US); Gregory M. Hyde, Menlo Park, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1432 days.

(21) Appl. No.: 11/008,902

(22) Filed: Dec. 10, 2004

(51) Int. Cl.
*A61F 2/24* (2006.01)
(52) U.S. Cl. ........ 623/2.36; 623/1.11; 604/263; 604/173
(58) Field of Classification Search .......................... None
See application file for complete search history.

(56) References Cited

U.S. PATENT DOCUMENTS

| | | | |
|---|---|---|---|
| 3,716,058 A | 2/1973 | Tanner et al. | |
| 4,719,924 A | 1/1988 | Crittenden et al. | |
| 4,781,186 A | 11/1988 | Simpson et al. | |
| 4,830,003 A * | 5/1989 | Wolff et al. | 606/191 |
| 4,830,023 A | 5/1989 | de Toledo et al. | |
| 4,920,980 A | 5/1990 | Jackowski | |
| 4,927,421 A | 5/1990 | Goble et al. | |
| 4,932,962 A | 6/1990 | Yoon et al. | |
| 4,994,067 A | 2/1991 | Summers | |
| 5,040,548 A | 8/1991 | Yock | |
| 5,061,273 A | 10/1991 | Yock | |
| 5,100,418 A | 3/1992 | Yoon et al. | |
| 5,100,421 A | 3/1992 | Christoudias | |
| 5,102,421 A | 4/1992 | Anspach, Jr. | |
| 5,116,337 A | 5/1992 | Johnson | |
| 5,129,902 A | 7/1992 | Goble et al. | |
| 5,141,520 A | 8/1992 | Goble et al. | |
| 5,156,616 A | 10/1992 | Meadows et al. | |
| 5,163,903 A * | 11/1992 | Crittenden et al. | 604/103.09 |
| 5,171,233 A | 12/1992 | Amplatz et al. | |
| 5,234,443 A | 8/1993 | Phan et al. | |
| 5,242,456 A | 9/1993 | Nash et al. | |

(Continued)

FOREIGN PATENT DOCUMENTS

DE 10161543 A1 6/2003

(Continued)

OTHER PUBLICATIONS

Messas, et al., "Chordal Cutting a New Therapeutic Approach for Ischmic Mitral Regurgitaion," 2001, American Heart Association Inc., pp. 1958-1963.

(Continued)

*Primary Examiner* — Corrine M McDermott
*Assistant Examiner* — Rebecca Straszheim
(74) *Attorney, Agent, or Firm* — Jonathan Feuchtwang; Blakely Sokoloff Taylor & Zafman LLP

(57) ABSTRACT

A method for placing a device into a target vasculature. The method comprises accessing the target vasculature with an access guide catheter to sub-select a proximal portion of the target vasculature. A rail catheter is tracked into the access guide catheter to place the rail catheter more distally and into a distal portion of the target vasculature. The access guide catheter is removed. A delivery catheter is tracked over the rail catheter. The rail catheter is then removed. A device catheter having the device is placed into the delivery catheter and positioned at a desired location within the distal portion of the target vasculature.

17 Claims, 11 Drawing Sheets

U.S. PATENT DOCUMENTS

| | | | |
|---|---|---|---|
| 5,246,441 | A | 9/1993 | Ross et al. |
| 5,350,395 | A | 9/1994 | Yock |
| 5,358,479 | A | 10/1994 | Wilson |
| 5,370,662 | A | 12/1994 | Stone et al. |
| 5,374,275 | A | 12/1994 | Bradley et al. |
| 5,383,260 | A | 1/1995 | Deschenes et al. |
| 5,431,673 | A | 7/1995 | Summers et al. |
| 5,441,483 | A | 8/1995 | Avitall |
| 5,451,233 | A | 9/1995 | Yock |
| 5,456,667 | A | 10/1995 | Ham et al. |
| 5,487,757 | A | 1/1996 | Truckai et al. |
| 5,495,974 | A | 3/1996 | Deschenes et al. |
| 5,518,162 | A | 5/1996 | Deschenes et al. |
| 5,520,700 | A | 5/1996 | Beyar et al. |
| 5,522,873 | A | 6/1996 | Jackman et al. |
| 5,531,686 | A | 7/1996 | Lundquist et al. |
| 5,554,184 | A | 9/1996 | Machiraju |
| 5,569,277 | A | 10/1996 | Evans et al. |
| 5,571,215 | A | 11/1996 | Sterman et al. |
| 5,588,188 | A | 12/1996 | Jermyn, Jr. |
| 5,609,598 | A | 3/1997 | Laufer et al. |
| 5,613,937 | A | 3/1997 | Garrison et al. |
| 5,617,854 | A | 4/1997 | Munsif |
| 5,626,613 | A | 5/1997 | Schmieding |
| 5,632,754 | A | 5/1997 | Farley et al. |
| 5,640,955 | A | 6/1997 | Ockuly et al. |
| 5,642,736 | A | 7/1997 | Avitall |
| 5,643,319 | A | 7/1997 | Green et al. |
| 5,681,280 | A | 10/1997 | Rusk et al. |
| 5,681,346 | A | 10/1997 | Orth et al. |
| 5,682,906 | A | 11/1997 | Sterman et al. |
| 5,687,723 | A | 11/1997 | Avitall |
| 5,709,224 | A | 1/1998 | Behl et al. |
| 5,728,129 | A | 3/1998 | Summers |
| 5,782,828 | A | 7/1998 | Chen et al. |
| 5,810,869 | A * | 9/1998 | Kaplan et al. ............... 606/194 |
| 5,810,882 | A | 9/1998 | Bolduc et al. |
| 5,823,955 | A | 10/1998 | Kuck et al. |
| 5,824,008 | A | 10/1998 | Bolduc et al. |
| 5,865,800 | A | 2/1999 | Mirarchi et al. |
| 5,868,733 | A | 2/1999 | Ockuly et al. |
| 5,868,767 | A | 2/1999 | Farley et al. |
| 5,916,213 | A | 6/1999 | Haissaguerre et al. |
| 5,954,731 | A | 9/1999 | Yoon |
| 5,961,440 | A | 10/1999 | Schweich, Jr. et al. |
| 5,964,772 | A | 10/1999 | Bolduc et al. |
| 5,972,022 | A | 10/1999 | Huxel |
| 5,989,284 | A | 11/1999 | Laufer |
| 6,001,095 | A | 12/1999 | de la Rama et al. |
| 6,001,104 | A | 12/1999 | Benderev et al. |
| 6,001,127 | A | 12/1999 | Schoon et al. |
| 6,004,332 | A | 12/1999 | Yoon et al. |
| 6,017,358 | A | 1/2000 | Yoon et al. |
| 6,021,340 | A | 2/2000 | Randolph et al. |
| 6,027,514 | A | 2/2000 | Stine |
| 6,036,715 | A | 3/2000 | Yock |
| 6,045,497 | A | 4/2000 | Schweich, Jr. et al. |
| 6,050,936 | A | 4/2000 | Schweich, Jr. et al. |
| 6,051,008 | A | 4/2000 | Saadat et al. |
| 6,059,715 | A | 5/2000 | Schweich, Jr. et al. |
| 6,077,214 | A | 6/2000 | Mortier et al. |
| 6,090,096 | A | 7/2000 | St. Goar et al. |
| 6,093,199 | A | 7/2000 | Brown et al. |
| 6,110,100 | A | 8/2000 | Talpade |
| 6,113,609 | A | 9/2000 | Adams |
| 6,117,176 | A | 9/2000 | Chen |
| 6,120,520 | A | 9/2000 | Saadat et al. |
| 6,123,699 | A | 9/2000 | Webster, Jr. |
| 6,149,669 | A | 11/2000 | Li |
| 6,161,543 | A | 12/2000 | Cox et al. |
| 6,162,168 | A | 12/2000 | Schweich, Jr. et al. |
| 6,164,283 | A | 12/2000 | Lesh |
| 6,165,119 | A | 12/2000 | Schweich, Jr. et al. |
| 6,165,120 | A | 12/2000 | Schweich, Jr. et al. |
| 6,165,164 | A | 12/2000 | Hill et al. |
| 6,165,183 | A | 12/2000 | Kuehn et al. |
| 6,165,197 | A | 12/2000 | Yock |
| 6,174,323 | B1 | 1/2001 | Biggs et al. |
| 6,176,240 | B1 | 1/2001 | Nikolchev et al. |
| 6,178,346 | B1 | 1/2001 | Amundson et al. |
| 6,179,840 | B1 | 1/2001 | Bowman |
| 6,182,664 | B1 | 2/2001 | Cosgrove |
| 6,183,411 | B1 | 2/2001 | Mortier et al. |
| 6,187,040 | B1 | 2/2001 | Wright |
| 6,190,401 | B1 | 2/2001 | Green et al. |
| 6,190,408 | B1 | 2/2001 | Melvin |
| 6,203,531 | B1 | 3/2001 | Ockuly et al. |
| 6,210,407 | B1 | 4/2001 | Webster, Jr. |
| 6,210,432 | B1 | 4/2001 | Solem et al. |
| 6,231,561 | B1 | 5/2001 | Frazier et al. |
| 6,231,587 | B1 | 5/2001 | Makower |
| 6,241,728 | B1 | 6/2001 | Gaiser et al. |
| 6,254,568 | B1 | 7/2001 | Ponzi |
| 6,254,598 | B1 | 7/2001 | Edwards et al. |
| 6,260,552 | B1 | 7/2001 | Mortier et al. |
| 6,261,222 | B1 | 7/2001 | Schweich, Jr. et al. |
| 6,264,602 | B1 | 7/2001 | Mortier et al. |
| 6,267,781 | B1 | 7/2001 | Tu |
| 6,269,819 | B1 | 8/2001 | Oz et al. |
| 6,270,526 | B1 | 8/2001 | Cox |
| 6,283,127 | B1 | 9/2001 | Sterman et al. |
| 6,283,962 | B1 | 9/2001 | Tu et al. |
| 6,290,674 | B1 | 9/2001 | Roue et al. |
| 6,299,622 | B1 | 10/2001 | Snow et al. |
| 6,306,133 | B1 | 10/2001 | Tu et al. |
| 6,312,447 | B1 | 11/2001 | Grimes |
| 6,325,823 | B1 | 12/2001 | Horzewski et al. |
| 6,355,030 | B1 | 3/2002 | Aldrich et al. |
| 6,371,978 | B1 | 4/2002 | Wilson |
| 6,374,476 | B1 | 4/2002 | Ponzi et al. |
| 6,402,780 | B2 | 6/2002 | Williamson, IV et al. |
| 6,402,781 | B1 | 6/2002 | Langberg et al. |
| 6,408,214 | B1 | 6/2002 | Williams et al. |
| 6,419,696 | B1 | 7/2002 | Ortiz et al. |
| 6,436,110 | B2 | 8/2002 | Bowman et al. |
| 6,447,517 | B1 | 9/2002 | Bowman |
| 6,461,366 | B1 | 10/2002 | Seguin |
| 6,482,224 | B1 | 11/2002 | Michler et al. |
| 6,488,689 | B1 | 12/2002 | Kaplan et al. |
| 6,493,575 | B1 | 12/2002 | Kesten et al. |
| 6,497,707 | B1 | 12/2002 | Bowman et al. |
| 6,500,167 | B1 | 12/2002 | Webster, Jr. |
| 6,537,198 | B1 | 3/2003 | Vidlund et al. |
| 6,537,314 | B2 | 3/2003 | Langberg et al. |
| 6,551,271 | B2 | 4/2003 | Nguyen |
| 6,554,794 | B1 | 4/2003 | Mueller et al. |
| 6,554,852 | B1 | 4/2003 | Oberlander |
| 6,575,998 | B2 | 6/2003 | Beyar |
| 6,585,718 | B2 | 7/2003 | Hayzelden et al. |
| 6,599,311 | B1 | 7/2003 | Biggs et al. |
| 6,605,086 | B2 | 8/2003 | Hayzelden et al. |
| 6,606,515 | B1 * | 8/2003 | Windheuser et al. ......... 600/434 |
| 6,610,058 | B2 | 8/2003 | Flores |
| 6,619,291 | B2 | 9/2003 | Hlavka et al. |
| 6,626,899 | B2 | 9/2003 | Houser et al. |
| 6,626,930 | B1 | 9/2003 | Allen et al. |
| 6,629,534 | B1 | 10/2003 | St. Goar et al. |
| 6,638,289 | B1 | 10/2003 | Burbank et al. |
| 6,648,903 | B1 | 11/2003 | Pierson, III |
| 6,656,221 | B2 | 12/2003 | Taylor et al. |
| 6,676,702 | B2 | 1/2004 | Mathis |
| 6,706,065 | B2 | 3/2004 | Langberg et al. |
| 6,709,442 | B2 | 3/2004 | Miller et al. |
| 6,709,456 | B2 | 3/2004 | Langberg et al. |
| 6,712,804 | B2 | 3/2004 | Roue et al. |
| 6,718,985 | B2 | 4/2004 | Hlavka et al. |
| 6,719,767 | B1 | 4/2004 | Kimblad |
| 6,723,038 | B1 | 4/2004 | Schroeder |
| 6,733,500 | B2 | 5/2004 | Kelley et al. |
| 6,746,472 | B2 | 6/2004 | Frazier et al. |
| 6,755,812 | B2 | 6/2004 | Peterson et al. |
| 6,761,734 | B2 | 7/2004 | Suhr |
| 6,764,510 | B2 | 7/2004 | Vidlund et al. |
| 6,770,070 | B1 | 8/2004 | Balbierz |
| 6,790,231 | B2 | 9/2004 | Liddicoat et al. |
| 6,800,090 | B2 | 10/2004 | Alferness et al. |
| 6,810,882 | B2 | 11/2004 | Langberg et al. |

| | | |
|---|---|---|
| 6,824,562 B2 | 11/2004 | Mathis et al. |
| 6,852,124 B2 | 2/2005 | Cox et al. |
| 6,890,353 B2 | 5/2005 | Cohn et al. |
| 6,905,476 B2 | 6/2005 | Ponzi |
| 6,908,478 B2 | 6/2005 | Alferness et al. |
| 6,911,035 B1 | 6/2005 | Blomme |
| 6,951,549 B1 | 10/2005 | Beyerlein |
| 6,960,229 B2 | 11/2005 | Mathis et al. |
| 6,964,683 B2 | 11/2005 | Kowalsky et al. |
| 6,966,926 B2 | 11/2005 | Mathis |
| 6,989,028 B2 | 1/2006 | Lashinski et al. |
| 6,997,951 B2 * | 2/2006 | Solem et al. ............ 623/2.37 |
| 7,073,504 B2 | 7/2006 | Callister et al. |
| 7,087,064 B1 | 8/2006 | Hyde |
| 7,104,999 B2 | 9/2006 | Overaker |
| 7,160,318 B2 | 1/2007 | Greenberg et al. |
| 7,186,264 B2 | 3/2007 | Liddicoat et al. |
| 7,247,149 B2 | 7/2007 | Beyerlein |
| 7,364,567 B2 | 4/2008 | Beyerlein |
| 2001/0003986 A1 | 6/2001 | Cosgrove |
| 2001/0005787 A1 | 6/2001 | Oz et al. |
| 2001/0018611 A1 | 8/2001 | Solem et al. |
| 2001/0027322 A1 | 10/2001 | Bowman |
| 2001/0044568 A1 | 11/2001 | Langberg et al. |
| 2002/0010483 A1 | 1/2002 | Folmer et al. |
| 2002/0010486 A1 | 1/2002 | Hirt |
| 2002/0013571 A1 | 1/2002 | Goldfarb et al. |
| 2002/0016628 A1 | 2/2002 | Langberg et al. |
| 2002/0026216 A1 | 2/2002 | Grimes |
| 2002/0035361 A1 | 3/2002 | Houser et al. |
| 2002/0042651 A1 | 4/2002 | Liddicoat et al. |
| 2002/0077647 A1 | 6/2002 | Snow et al. |
| 2002/0087169 A1 | 7/2002 | Brock et al. |
| 2002/0087173 A1 | 7/2002 | Alferness et al. |
| 2002/0103492 A1 | 8/2002 | Kaplan et al. |
| 2002/0103532 A1 | 8/2002 | Langberg et al. |
| 2002/0103533 A1 | 8/2002 | Langberg et al. |
| 2002/0111637 A1 | 8/2002 | Kaplan et al. |
| 2002/0161330 A1 | 10/2002 | Nguyen |
| 2002/0165484 A1 | 11/2002 | Bowe et al. |
| 2002/0165533 A1 | 11/2002 | Flores |
| 2002/0165534 A1 | 11/2002 | Hayzelden et al. |
| 2002/0169502 A1 | 11/2002 | Mathis |
| 2002/0169504 A1 | 11/2002 | Alferness et al. |
| 2002/0183835 A1 | 12/2002 | Taylor et al. |
| 2002/0183836 A1 | 12/2002 | Liddicoat et al. |
| 2002/0183837 A1 | 12/2002 | Streeter et al. |
| 2002/0183841 A1 | 12/2002 | Cohn et al. |
| 2002/0188170 A1 | 12/2002 | Santamore et al. |
| 2003/0050598 A1 | 3/2003 | Hayzelden et al. |
| 2003/0069593 A1 | 4/2003 | Tremulis et al. |
| 2003/0078465 A1 | 4/2003 | Pai et al. |
| 2003/0083538 A1 | 5/2003 | Adams et al. |
| 2003/0088195 A1 * | 5/2003 | Vardi et al. ............ 600/585 |
| 2003/0093071 A1 | 5/2003 | Hauck et al. |
| 2003/0105520 A1 | 6/2003 | Alferness et al. |
| 2003/0120340 A1 | 6/2003 | Liska et al. |
| 2003/0120341 A1 | 6/2003 | Shennib et al. |
| 2003/0130731 A1 | 7/2003 | Vidlund et al. |
| 2003/0144697 A1 | 7/2003 | Mathis |
| 2003/0144732 A1 | 7/2003 | Cosgrove et al. |
| 2003/0163118 A1 * | 8/2003 | Hamilton et al. ............ 604/525 |
| 2003/0167071 A1 | 9/2003 | Martin et al. |
| 2003/0171776 A1 | 9/2003 | Adams et al. |
| 2003/0212453 A1 | 11/2003 | Mathis et al. |
| 2003/0216764 A1 | 11/2003 | Tu et al. |
| 2004/0010231 A1 | 1/2004 | Leonhardt et al. |
| 2004/0044350 A1 | 3/2004 | Martin et al. |
| 2004/0044365 A1 | 3/2004 | Bachman |
| 2004/0045463 A1 | 3/2004 | Pertile |
| 2004/0049207 A1 | 3/2004 | Goldfarb et al. |
| 2004/0059531 A1 | 3/2004 | Eigler et al. |
| 2004/0098092 A1 | 5/2004 | Butaric et al. |
| 2004/0138683 A1 | 7/2004 | Shelton et al. |
| 2004/0138744 A1 | 7/2004 | Lashinski et al. |
| 2004/0148020 A1 | 7/2004 | Vidlund et al. |
| 2004/0153147 A1 | 8/2004 | Mathis |
| 2005/0045183 A1 | 3/2005 | Callister et al. |
| 2005/0055089 A1 | 3/2005 | Macoviak et al. |
| 2005/0085844 A1 | 4/2005 | Tremulis et al. |
| 2005/0209633 A1 | 9/2005 | Callister et al. |
| 2005/0267571 A1 | 12/2005 | Spence et al. |
| 2005/0267573 A9 | 12/2005 | Macoviak et al. |
| 2006/0041306 A1 | 2/2006 | Vidlund et al. |
| 2006/0095025 A1 | 5/2006 | Levine et al. |
| 2006/0282161 A1 * | 12/2006 | Huynh et al. ............ 623/2.11 |

FOREIGN PATENT DOCUMENTS

| | | |
|---|---|---|
| EP | 0377269 A1 | 7/1990 |
| WO | WO 98/029041 A1 | 7/1998 |
| WO | WO 99/000059 | 1/1999 |
| WO | WO 99/013777 | 3/1999 |
| WO | WO 99/30647 A1 | 6/1999 |
| WO | WO 99/44534 A1 | 9/1999 |
| WO | WO 00/03759 | 1/2000 |
| WO | WO 00/06026 A2 | 2/2000 |
| WO | WO 00/06027 A2 | 2/2000 |
| WO | WO 00/06028 A1 | 2/2000 |
| WO | WO 00/16700 A1 | 3/2000 |
| WO | WO 00/60995 | 10/2000 |
| WO | WO 01/00111 A1 | 1/2001 |
| WO | WO 01/00114 A1 | 1/2001 |
| WO | WO 01/26557 A1 | 4/2001 |
| WO | WO 01/28432 A2 | 4/2001 |
| WO | WO 01/28455 A1 | 4/2001 |
| WO | WO 01/49213 A2 | 7/2001 |
| WO | WO 01/49213 A3 | 7/2001 |
| WO | WO 01/54618 A1 | 8/2001 |
| WO | WO 01/89440 A2 | 11/2001 |
| WO | WO 02/00099 A2 | 1/2002 |
| WO | WO 02/01999 A2 | 1/2002 |
| WO | WO 02/34167 A2 | 5/2002 |
| WO | WO 02/39925 A2 | 5/2002 |
| WO | WO 0234167 | 5/2002 |
| WO | WO 02/053206 A2 | 7/2002 |
| WO | WO 02/060352 | 8/2002 |
| WO | WO 02/062263 A2 | 8/2002 |
| WO | WO 02/062270 A1 | 8/2002 |
| WO | WO 02/062408 A2 | 8/2002 |
| WO | WO 02/063533 | 8/2002 |
| WO | WO 02/078576 | 10/2002 |
| WO | WO 03/049619 A2 | 6/2003 |
| WO | WO 03/073913 A2 | 9/2003 |
| WO | WO 2004/012789 A2 | 2/2004 |
| WO | WO 2004/014282 A2 | 2/2004 |

OTHER PUBLICATIONS

Bonow, Robert O., et al., "Guidelines for the Management of Patients with Valvular Health Disease," Report of American College of Cardiology/American Heart Assoc. Task Force on Practice Guidelnes (Committee on Mangement of Pateints with Valvular Heart Disease), American College of Cardiology and American Heart Assoc., Inc., 1998, pp. 1949-1984.

PCT Invitation to Pay Additional fees for PCT International Appln. No. US03/36633, mailed May 19 2004 (5 pages).

PCT Report for PCT International Patent Application PCT/US2004/031403, mailed Jun. 15, 2005. 5 pgs.

PCT International Preliminary Report on Patentability and Written Opinion for PCT Appln No. US2004/031403, mailed Apr. 13, 2006 (8 pages).

PCT International Search Report and Written Opinion of the International Searching Authority for PCT Appln No. US2004/031403, mailed May 18, 2005 (14 pages).

PCT Search Report and Written Opinion for PCT/US2007/011948, mailed Nov. 16, 2007, 16 pages.

PCT Invitation to Pay Additional Fees for PCT International Appln. No. US2004/031403, mailed Feb. 15, 2005 (5 pages).

* cited by examiner

VASCULAR DELIVERY SYSTEM FOR ACCESSING AND DELIVERING DEVICES INTO CORONARY SINUS AND OTHER VASCULAR SITES

FIELD

Embodiments of the present invention pertain to a delivery system and method to provide access to the coronary sinus and its more distal communicating vessels or into other vascular sites via other entrance locations.

DISCUSSION OF RELATED ART

Percutaneous interventional therapeutic and diagnostic procedures are performed using devices that are placed inside lumens of the body. These devices are directed to the site of treatment by tracking them and/or their delivery systems over a guidewire using one of many methods of attachment to the guidewire. A few of such methods include rapid exchange (RX), over the wire (OTW), peel away or zipper methods. The basic technique is to track the therapeutic or diagnostic device through the body lumen by first placing a guidewire in the lumen past the site of interest and then sliding the device and/or its delivery system over the guidewire until the device is at or across the desire location of therapy and/or diagnostic interest.

There are generally two ways of delivering a device into a vessel. In a first method, a guidewire is inserted into the vessel. A catheter housing or incorporating the device is configured such that the catheter and/or the device can engage the guidewire. Examples of such a catheter system include an over the wire catheter system or a rapid exchange catheter system. In the over the wire catheter system, the entire catheter engages the guidewire and the catheter is configured with a lumen for the guidewire wherein the lumen extends the entire length of the catheter and the guidewire is tracked inside the lumen. In the rapid exchange catheter system, only a distal section of the catheter includes a lumen for the guidewire and the guidewire engages the catheter only at the distal section. In a second method, the device is delivered to the vessel via the inner diameter of a catheter, usually a guide catheter. Because the outer diameter of the catheter tracks along the inner diameter of the guide catheter, we will call this "outer diameter tracking". For example, a guide catheter is inserted into a peripheral vessel such that its distal end is proximal to a desired location and the catheter housing or incorporating the device is inserted within the guide catheter until it extends out the guide catheter's distal end. These two methods are combined in most catheter delivery procedures. For example, in angioplasty or stent delivery procedures, the angioplasty or stent delivery catheter is delivered to the ostium of the coronary artery via the ID of a guide catheter and is further directed to the desired site within the coronary artery by a guidewire.

There is a need to improve the delivery of percutaneous therapeutic and/or diagnostic devices through a method of outer diameter tracking. Outer diameter tracking is advantageous when delivering large devices, devices that require the vessel walls through which they are delivered to be well protected during the delivery of the device, or if the vessel to which the device is being delivered to is fragile or very compliant, such as a vein of the heart or a wall of the coronary sinus. In addition, some of the therapeutic and/or diagnostic devices and/or device delivery systems under consideration may not easily accommodate a guidewire, especially the larger guidewires, without a relatively large increase in their outer diameters (OD's), causing them to require unacceptably large introducer sheaths and/or be unacceptably large for the OD of the vessel in which they must be delivered and/or be unacceptably stiff for the distensibility of the vessels through which they must be delivered.

SUMMARY

Some aspects of the invention embodiments pertain to a method for placing a device into a target vasculature such as a sinus, a blood vessel, a vein, or an artery extending or stemming from an ostium, a proximal vessel or other vascular structure. The method comprises accessing the proximal portion of a target vasculature (e.g., an ostium, vessel branch or sinus) with an access guide catheter to sub-select a proximal portion of the target vasculature. The access guide catheter is essentially the same as a normal guide catheter and is used to access the proximal vasculature in the conventional manner. A rail catheter is tracked into the access guide catheter to place the rail catheter more distally into the accessed target vasculature and/or to sub-select more distal vessel branches at or across the regions of interest in the target vasculature. The access guide catheter is then removed over the rail catheter, leaving the rail catheter in place at or across the region of interest in the target vasculature. A delivery catheter is tracked over the rail catheter. The delivery catheter is similar in design to the access guide catheter, except it includes a more flexible section added to its distal end. This more flexible section of the delivery catheter is positioned over the rail catheter to reside across the target vasculature's (or other vascular structures) regions of interest. The rail catheter is then withdrawn and removed. A device or a device catheter housing, having or incorporating the device is inserted into the delivery catheter and positioned at a desired location within the target vasculature and within the flexible section of the delivery catheter. The delivery catheter may then be withdrawn over the device or the device catheter housing, having, or incorporating the device to expose the desired portions of the device to the target vasculature.

In other aspects, a method for placing a device into a target vasculature comprises accessing a peripheral vessel lumen that leads to the target vasculature with an introducer sheath and an access guide catheter. The introducer sheath accesses the peripheral vessel lumen and the access guide catheter sub-selects a proximal portion of the target vasculature. The target vasculature can be a vessel branch of the vessel lumen, a sinus stemming from the vessel lumen, a vasculature structure communicating with the vessel lumen (e.g., a chamber of the heart) or a vasculature structure communicating with the vessel lumen that is proximate or adjacent to a treatment site. A guidewire is inserted into the access guide catheter and is placed across the more distal portions of the target vasculature. A rail catheter is tracked over the guidewire and within the access guide catheter and is placed across the more distal portions of the target vasculature. The guidewire is removed. The access guide catheter is then removed over the rail catheter, leaving the rail catheter in place. A delivery catheter is tracked over the rail catheter. The rail catheter is removed. A device or a device catheter housing, having, or incorporating the device is inserted into the delivery catheter and positioned at a desired location within the target vasculature and within the delivery catheter. The delivery catheter is then withdrawn to expose the desired portions of the device to the target vasculature.

In other aspects, a method for placing a device into a distal portion of a target vasculature comprises accessing a peripheral or more proximal vessel lumen that leads to the target vasculature with an introducer sheath and an access guide catheter. The introducer sheath accesses the peripheral or more proximal vessel lumen and the access guide catheter sub-selects a proximal portion of the target vasculature. The target vasculature can be a vessel branch of the vessel lumen, a sinus stemming from the vessel lumen, a vascular structure communicating with the vessel lumen (e.g., a chamber of the heart), or a vasculature structure communicating with the vessel lumen that is proximate or adjacent to a treatment site. A rail catheter having a guidewire disposed therein is inserted into the access guide catheter. The rail catheter together with the guidewire is used to sub-select or access more distal portions of the target vasculature. Additionally, in embodiments where the rail catheter is too stiff or too difficult to travel or make function in the target anatomy, the guidewire may be advanced to perform sub-selection or gain more distal vessel access into the more distal portions of the target vasculature and then the rail catheter may be advanced over the guidewire to secure the sub-selection and/or gain more access distally. In embodiments where the rail catheter is sufficient to reach the more distal portions of the target vasculature, the guidewire may be omitted entirely. The method further comprises injecting contrast into the target vasculature to fluoroscopically visualize a treatment location or region of interest. The injection of the contrast also provides a way to determine the length(s), separations(s) and/or diameter(s) of the treatment location in the target vasculature. Other visualization or imaging techniques may also be used or substituted (e.g., MRI and ultrasound) with appropriate visualization and measurement aids or markers incorporated on the guidewire and/or the rail catheter. In one embodiment, the rail catheter and/or the guidewire may be provided with markers such as radiopaque markers at known and/or equal intervals. The markers provide a way to determine lengths in the treatment location. The guidewire may then be removed from the rail catheter. Then, the access guide catheter is removed over the rail catheter, leaving the rail catheter in place. A delivery catheter having a flexible distal end is tracked over the rail catheter. The flexible distal end of the delivery catheter may have a length and/or other properties (e.g., diameters, flexibility, or shape) selected based on the previous measurements and visualization of the target vasculature. The rail catheter is removed. A device or a device catheter housing, having or incorporating the device is inserted into the delivery catheter and positioned at a desired location within the target vasculature and within the delivery catheter. The delivery catheter is then withdrawn over the device or the device catheter housing, having, or incorporating the device to expose desired portions of the device to the target vasculature. The device or the device catheter housing, having, or incorporating the device may have a length(s) and/or a diameter(s) that are related to or chosen based on the treatment location or region of interest length(s), separations and/or diameters as previously determined.

Other aspects pertain to methods for treating a Mitral valve, which comprise accessing a coronary sinus (e.g., at the entrance of the coronary sinus) with an introducer sheath and access guide catheter. A rail catheter is tracked into the access guide catheter to place the rail catheter into a treatment site such as distal portions of the coronary sinus, the great cardiac vein and/or other distal veins stemming from the coronary sinus or cardiac structures associated with the coronary sinus. The access guide catheter is removed over the rail catheter, leaving the rail catheter in place. A delivery catheter is tracked over the rail catheter. The rail catheter is removed and a Mitral valve repair device is inserted into the delivery catheter and positioned at the treatment site such as the distal portion of the coronary sinus, the great cardiac vein, or other distal veins stemming from the coronary sinus, or cardiac structures associated with the coronary sinus. The Mitral valve repair device may be housed in its own delivery system. The delivery catheter is then withdrawn to expose the desired portions of the Mitral valve repair device to the treatment site. The Mitral valve repair device is deployed within the treatment site. In some embodiments, the Mitral valve repair device (and/or its delivery system) may be re-positioned within the treatment site and the delivery catheter, after which the delivery catheter is further withdrawn to expose a more proximal section of the Mitral valve repair device to the treatment site and in some embodiments, to allow another deployment of another portion of the device. A Mitral valve repair device or other device may require one or more deployments or exposures at different locations or treatment sites within the vascular system. In several embodiments, the Mitral valve repair device is placed or deployed in the coronary sinus or cardiac structures associated with the coronary sinus to treat a Mitral valve that is adjacent or proximate the coronary sinus or associated cardiac structure.

Other aspects pertain to a medical device which comprises an access guide catheter configured with an access port and configured to enable a fluid injection; a rail catheter disposed within the access guide catheter, the rail catheter having a distal tip section, a distal body section, a transition section, and a proximal section; and a central lumen extending provided within the distal tip section and the transition section of the rail catheter and extending at least therethrough. The proximal section of the rail catheter has an outer diameter that is smaller than an outer diameter of the distal body section of the rail catheter, and the outer diameter of the distal body section is closely fitted within an inner diameter of the access guide catheter. The transition section of the rail catheter preferably being beveled.

BRIEF DESCRIPTION OF THE DRAWINGS

The present invention is illustrated by way of example and not limitation in the figures of the accompanying drawings, in which like references indicate similar elements and in which.

DETAILED DESCRIPTION

The exemplary embodiments of the present invention pertain to a delivery method and delivery system for accessing vessels, distal portions of vessels, branches of vessels such as veins, arteries, coronary sinuses, great cardiac veins, or other vascular structures. The exemplary embodiments of the present invention also pertain to a delivery method and a delivery system for delivering a device, such as a diagnostic device, a therapeutic device, and other medical devices into a body lumen or a target vasculature such as vein or vessel such as the great cardiac vein and/or vascular structure such as the coronary sinus. Examples of such devices include a Mitral valve repair device, a catheter, and a pacemaker lead. The exemplary embodiments of the present invention also pertain to a medical device or a kit that treats the Mitral valve and is deliverable into the coronary sinus and/or more distal communicating vessels or veins. Throughout the document, the words "target vasculature," "treatment site," and "treatment area" are used to refer at least to vessels, branches of vessels, veins, arteries, sinuses, coronary sinuses, great cardiac veins, or other vascular structures that a device needs to be delivered to for a particular purpose, e.g., therapeutic, diagnostic, or the like. For example, a treatment area or site may be a portion of the coronary sinus that may impact or otherwise exert pressure on the Mitral valve adjacent the coronary sinus so that a Mitral valve repair device can be delivered to the treatment area to help repair the Mitral valve.

In the following description, for purposes of explanation, numerous specific details are set forth in order to provide a thorough understanding of the present invention. It will be evident, however, to one skilled in the art, that the present invention may be practiced without these specific details. In other instances, specific apparatus structures and methods have not been described so as not to obscure the present invention. The following description and drawings are illustrative of the invention and are not to be construed as limiting the invention.

Figure 1A:
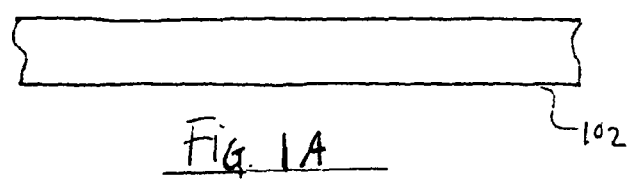
FIGS. 1A-1L illustrates conventional ways of accessing a target vasculature vessel and delivering a device into the target vasculature.
Figure 1B:
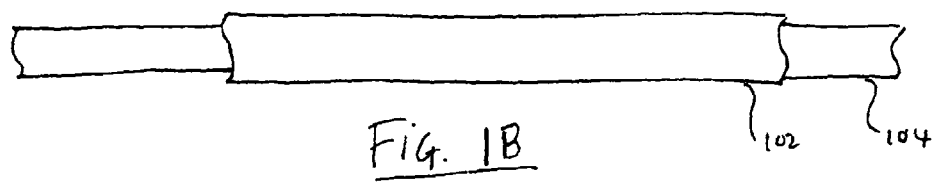
Figure 1C:
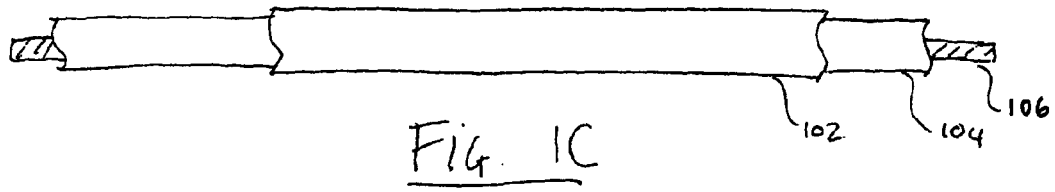
Figure 1D:
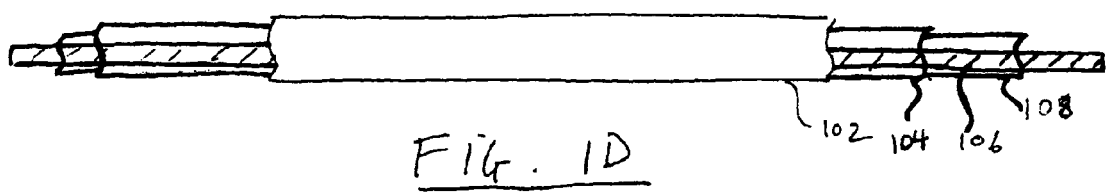

The conventional way of accessing a vessel, such as a coronary artery, vein or sinus, is well known in the art. First, access to a peripheral vessel is established percutaneously with an introducer sheath 102 (FIG. 1A). Next, a guide catheter 104 is inserted into the inner diameter (ID) of the introducer sheath 102 (FIG. 1B) and further distally into the vessel to provide access to the vessel, a vessel branch or other communicating vascular structure proximal of the region of interest. Contrast may be injected into the vessel via the guide catheter to provide fluoroscopic visualization of the vascular anatomy. The access devices commonly contain radiopaque portions or are radiopaque to allow them to also be fluoroscopically visualized and thus, guided more effectively. A 0.014" OD guidewire 106 is inserted into the guide catheter 104 and out into the vascular anatomy (FIG. 1C). The guidewire 106 is used to navigate and sub-select vessels and structures distal to the guide catheter 104 that would be too small, difficult or dangerous to attempt to navigate with the guide catheter 104. Guide catheters are commonly relatively stiff (compared to guidewires) and have pre-shaped ends that aid in obtaining and retaining access to particular ostium, proximal vessel, sinus or other vascular anatomies. Once the guidewire 106 is across the vascular region of interest, a relatively less stiff (than the guide catheter 104) catheter 108 is engaged with the guidewire 106 and is inserted into the guide catheter 104 and further inserted until it is distal to the guide catheter 104 (FIG. 1D) and, following the guidewire 106, positioned in the vascular anatomy at the position of interest or across the region of interest. At that time, the catheter 108 may be used to perform its diagnostic and/or therapeutic functions.

Figure 1E:
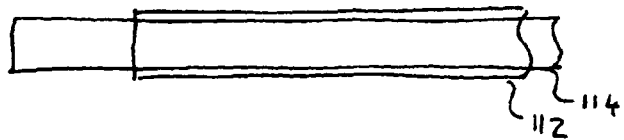
Figure 1F:
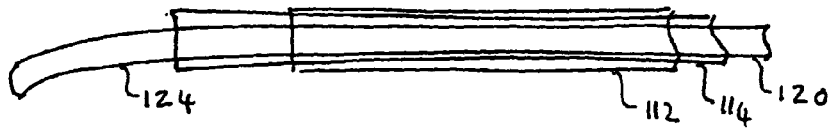
Figure 1G:
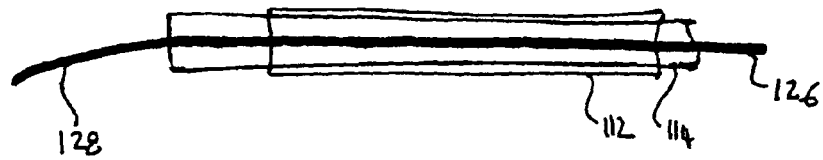
Figure 1H:
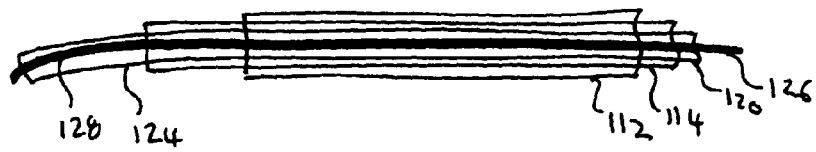
Figure 1I:
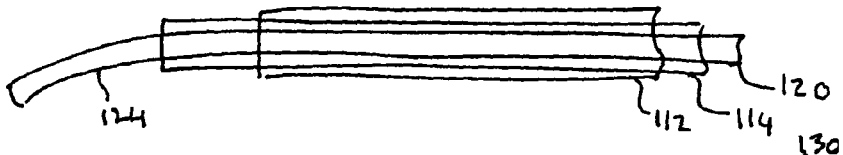
Figure 1J:
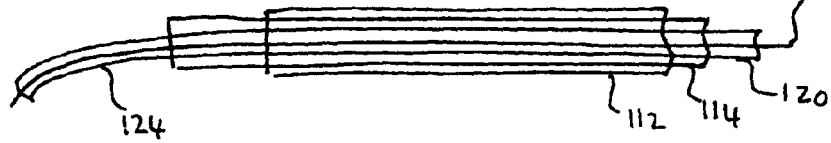
Figure 1K:
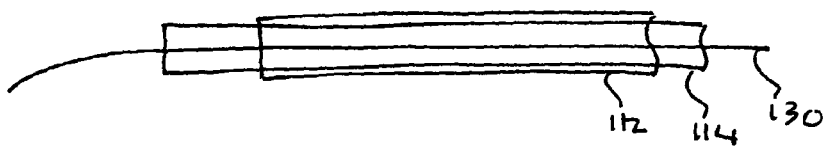
Figure 1L:
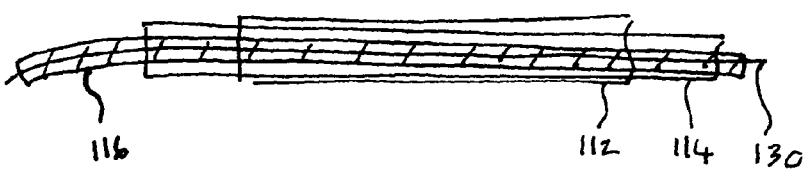

More recently, another method (FIGS. 1E-1L) has been developed specifically for accessing the coronary sinus to implant a medical device 116 such as a pacing lead. As before, an introducer sheath 112 and a guide catheter (FIG. 1E) (an outer guide catheter 114) are used to gain access to the proximal portion of the coronary sinus, or the ostium of the coronary sinus, where the coronary sinus empties into the right atrium. Access to this ostium can be very difficult despite the pre-shape on the distal end of the outer guide catheter 114, so a more flexible inner guide catheter 120 is inserted inside the outer guide catheter 114 and out its distal end (FIG. 1F). This flexible inner guide catheter 120 usually has a bend on its distal end 124 to aid in accessing the coronary sinus ostium at different angles and later for sub-selecting and navigating more distally into the coronary sinus and its branching veins. Even this more flexible inner guide catheter 120 sometimes has difficulty navigating and sub-selecting the more distal vascular anatomy, so a large guidewire 126 (usually with an outer diameter (OD) in the range of 0.020" to 0.0040"), often with a bent distal end 128, may be used to sub-select and gain access further distally (FIG. 1G). The flexible inner guide catheter 120 is then advanced over the large guidewire 126 (FIG. 1H) to secure the sub-selection and access; then the large guidewire 126 is withdrawn (FIG. 1I). The outer guide catheter 114 may be advanced over the flexible inner guide catheter 120 to help secure the access to the sinus for the outer guide catheter 114 either before or after the large guidewire 126 is withdrawn. A smaller guidewire 130 (e.g., 0.014" guidewire) is then inserted into the flexible inner guide catheter 120 and out its distal end into the vessel the desired distance (FIG. 1J). The flexible inner guide catheter 120 is then withdrawn, leaving the smaller guidewire 130 and the outer guide catheter 114 in place (FIG. 1K). The medical device, a pacing lead 116, is then inserted over the guidewire 130 and out of the outer guide catheter 114 into the desired position in the vessel (FIG. 1L). Once the pacing lead 116 is properly placed, the guidewire 130, the outer guide catheter 114 and the introducer sheath 112 are withdrawn.

Many catheter systems for medical devices, such as therapeutic catheters and even some diagnostic catheters are stiff and large and many need to be delivered into fragile and distensible sinus's, vessels or small branches of the vessels or other fragile and/or distensible target vasculature structures. Conventional access methods, such as those previously described, require these large and stiff catheter systems to enter fragile and distensible sinus's, small vessels or branches of vessels or other fragile and/or distensible target vasculature structures following a relatively small guidewire (e.g., 0.014" guidewire). However, many of these catheter systems are too large and/or stiff (or the distal portions of them are) to follow the relatively flexible 0.014" guidewire in many anatomies. The catheter systems become even larger and stiffer, if the larger and, therefore stiffer, guidewires are used to improve the ability of the catheter system to follow the guidewire. In some cases, the catheter systems become larger in OD than the desired anatomy location and, thus, cannot be safely delivered, even when they incorporate the smallest guidewire lumen (lumen for the 0.014" guidewire). When larger access devices are required, this causes an increase in complications at the introducer sheath insertion site. Additionally, the large and stiff catheter system is in direct contact with the fragile and distensible sinus, vascular wall or other fragile and distensible target vasculature structures during catheter system positioning, which can cause perforation or other damage to the vascular wall or the target vasculature wall. Vascular perforation can lead to death and vascular wall damage can lead to occlusion and/or thrombus emboli complications. Thus there is a need for a delivery system to provide access to anatomies such as the coronary sinus in a manner that protects the vascular system or the target vasculature walls during the positioning of large and/or stiff catheter systems and will allow these catheter systems to be positioned as desired in the anatomy. Additionally, there is a need to provide these benefits without causing the large and/or stiff catheter systems to become even larger and/or stiffer. Preferably, the delivery system would eliminate the need for these catheter systems to contain a guidewire lumen and, thus allow them to become smaller and less stiff.

Figure 2:
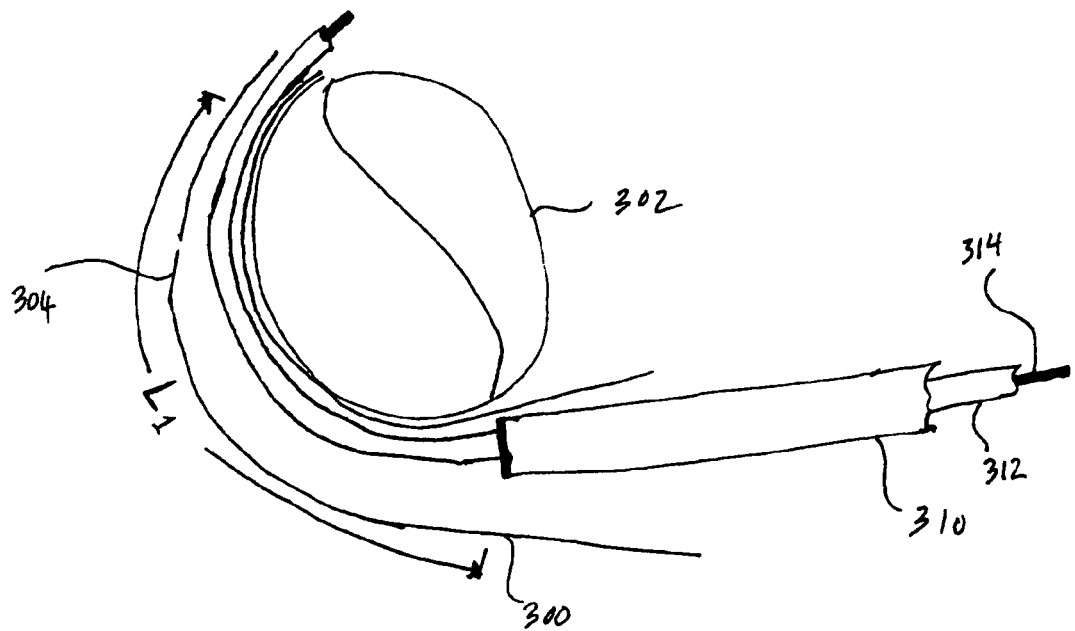
FIGS. 2-5 illustrates an exemplary embodiment of a delivery system that can be used to deliver a device into a target vasculature.

FIGS. 2-5 illustrate an exemplary embodiment showing a delivery system (or a catheter system) that can be used to deliver a device (e.g., a Mitral valve repair device) into a target vasculature (e.g., a coronary sinus). The delivery system can be used to deliver the device to distal portions of the target vasculature (e.g., a great cardiac vein). First, a percutaneous access is made to a blood vessel lumen that leads to the target vasculature. The target vasculature, in one embodiment, is a coronary sinus 300 shown in FIGS. 2-5. In one embodiment, the percutaneous access provides a way for catheter systems to enter the target vasculature to deliver devices(s). Many of the embodiments discuss herein delivering devices and accessing the coronary sinus and/or the great cardiac vein as the target vasculature, but it is to be noted that the embodiments are similarly applicable to other target vasculatures, e.g., blood vessels, arteries, or veins. In one embodiment an introducer sheath (not shown) is used to percutaneously access the coronary sinus 300. In embodiments where the target vasculature is the coronary sinus 300, the introducer sheath is used to percutaneously access a peripheral vessel lumen that can lead to the coronary sinus 300. An access guide catheter 310 is inserted into the introducer sheath and into the peripheral vessel lumen to engage the coronary sinus 300. FIG. 2 illustrates the access guide catheter 310 engaging the coronary sinus 300 at the entrance of the coronary sinus.

Figure 3:
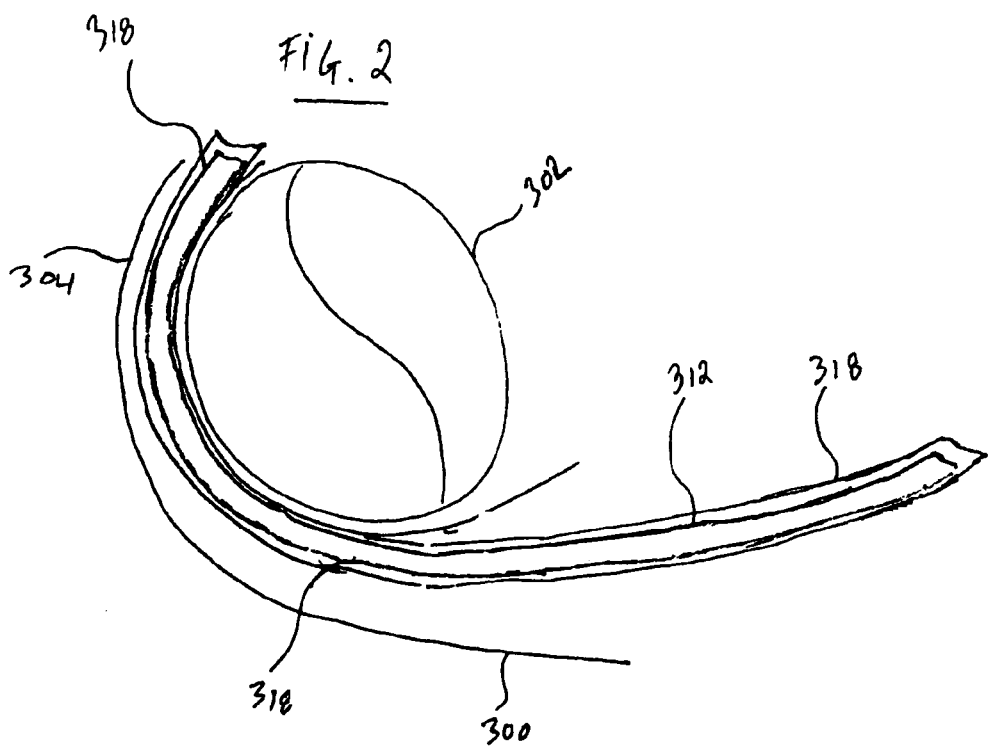

Next, a guidewire 314 is placed into the access guide catheter 310 to allow the guidewire 314 to access a distal portion of the coronary sinus or a portion of the great cardiac vein 304 (FIG. 2). Next, a rail catheter 312 is tracked over the guidewire 314, into the access guide catheter 310 and advanced to the great cardiac vein 304 (FIG. 2). The guidewire 314 is placed into the distal portion of the coronary sinus 300 to allow the delivery system to sub-select the more distal portion of the coronary sinus 300 or a portion of the great cardiac vein 304. Once the rail catheter 312 is inserted into the access guide catheter 310 and over the guidewire 314 to the distal portion of the coronary sinus 300, the guidewire 314 and then the access guide catheter 310 can be removed as shown in FIG. 3.

Figure 4:
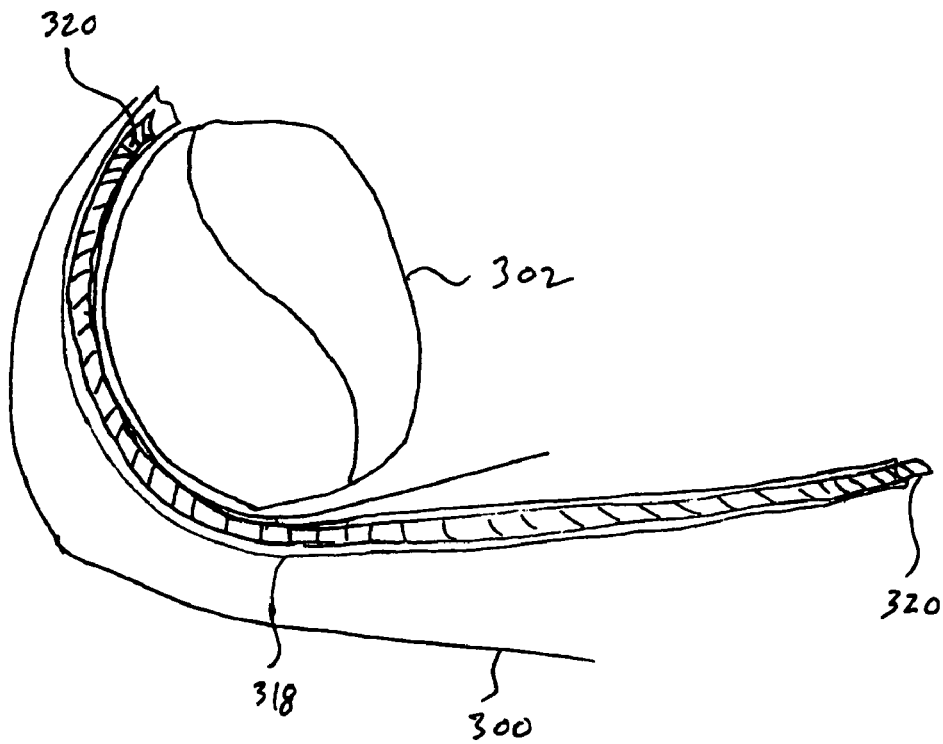

Next, a delivery catheter 318 is tracked over the rail catheter 312 and within the introducer sheath into the entrance of the coronary sinus 300 and placed distally in distal portions of the coronary sinus 300 or across a portion of the great cardiac vein 304. The rail catheter 312 and the delivery catheter 318 are placed in the portions of the coronary sinus 300 or great cardiac vein 304 where it is desirable to have a device deployed or placed therein (treatment site). The rail catheter 312 is then removed leaving the delivery catheter 318 within the introducer sheath and within the coronary sinus 300 (FIG. 4). In other embodiments, the guidewire 314 is removed at any time after the rail catheter 312 is in place. The delivery catheter 318 is configured to allow a device to be tracked there within. In one embodiment, the device is housed in a device catheter or a delivery/deployment system. A device 320 is inserted into the delivery catheter 318 as shown in FIG. 4. The device 320 can be selected from various types of devices such as a pacing lead or a device delivery system/catheter (e.g., a Mitral valve repair device and its delivery system). In one embodiment, the device 320 is a therapeutic device such as a Mitral valve repair device and its delivery system. The device 320 can also be a diagnostic device or a device that is both diagnostic and therapeutic. As shown in FIG. 4, the feature "320" may indicate a medical device or the medical device housed in its own delivery system or a device catheter.

In an alternative embodiment, the guidewire 314 is placed within the rail catheter 312 prior to the insertion of the rail catheter 312 within the access guide catheter 310. Thus, the rail catheter 312 having the guidewire 314 can be inserted into the access guide catheter 310 together as a unit to sub-select the distal portions of the coronary sinus 300 or a portion of the great cardiac vein 304.

Figure 5:
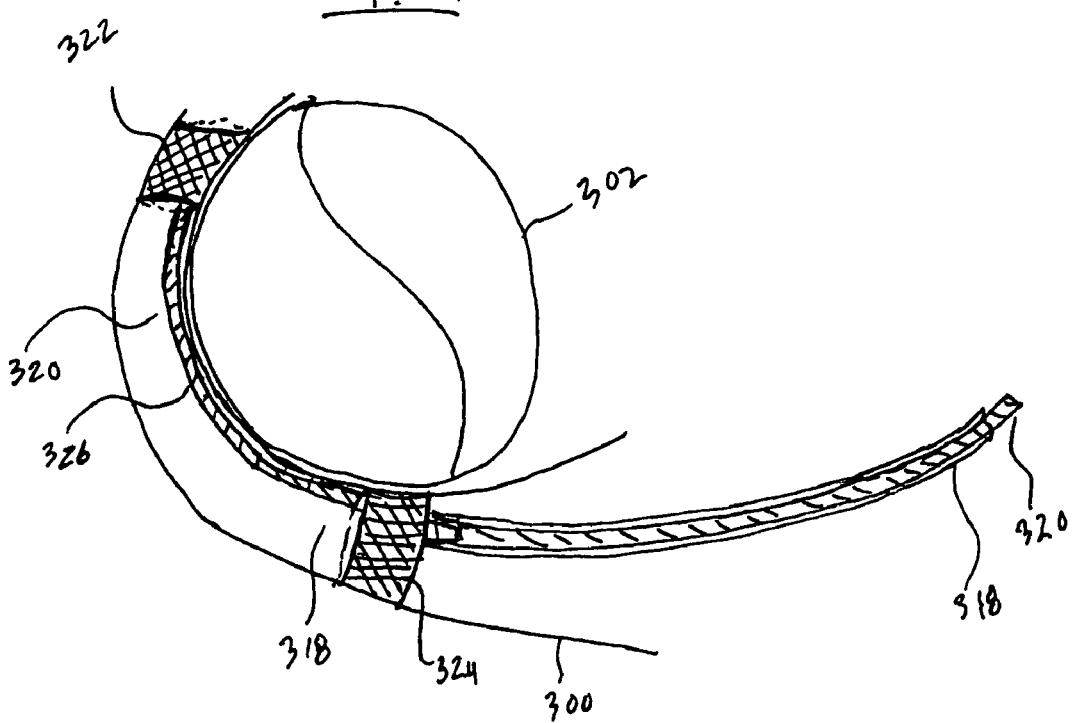

In one embodiment, the device 320 is deployed within the great cardiac vein 304 and coronary sinus 300 as shown in FIG. 5. In one embodiment, to deploy the device 320, the delivery catheter 318 is retracted proximally while the device 320 is held in place to expose the device 320 and to allow the device 320 to be deployed. The delivery catheter 318 continues to be retracted to allow device 320 to be completely deployed. The delivery catheter 318 and the introducer sheath are removed completely after the device 320 is deployed. The delivery catheter 318 may be removed prior to the removal of the introducer sheath. In the embodiments where the device 320 is housed in its own device delivery system/catheter, the device delivery system/catheter may need to be removed after the deployment of device 320 prior to the removal of the introducer sheath or even prior to the removal of the delivery catheter 318.

In one embodiment, the device 320 is a Mitral valve repair device that includes an expandable distal anchoring member 322 connected to an expandable proximal anchoring member 324 by a connecting device or a telescoping assembly 326. Note that the device 320 is shown in FIG. 5 in its deployed state. In one embodiment, when the delivery catheter 318 (and/or a portion of the device delivery system/catheter) is withdrawn, the distal anchoring member 322 and the proximal anchoring member 324 are expanded and anchored within the coronary sinus 300. The connecting device or the telescoping assembly 326 allows for adjustment of the distance between the distal anchoring member 322 and the proximal anchoring member 324, thus, allowing for reshaping of the Mitral valve 302. In one embodiment, the Mitral valve repair device is implantable or at least portions of the device are implantable. In embodiments where the device 320 is housed in the device delivery system/catheter, a portion of the device delivery system/catheter may need to be withdrawn to allow components of the device 320 to deploy. A portion of the device delivery system/catheter may be withdrawn to deploy the device after the delivery catheter 318 is withdrawn to expose the device 320 to the vasculature.

In another embodiment, the device 320 is an annuloplasty device such as those described in U.S. patent application Ser. No. 10/297,714, filed on Nov. 15, 2002 entitled "Apparatuses and Methods for Heart Valve Repair". In another embodiment, the device 320 is an annuloplasty device such as those described in U.S. patent application Ser. No. 10/740,360 filed on Dec. 17, 2003 entitled "A Cord Locking Mechanism for Use in Small Systems". The mentioned Applications are hereby incorporated by reference in their entirety. In many embodiments, the device 320 is capable of reshaping a Mitral valve annulus 302, which is adjacent to the coronary sinus 300. Reshaping includes at least reducing, reforming, or adjusting the Mitral valve annulus 302 in a way that cause the leaflets of the Mitral valve to move closer to each other. Reshaping may also include increasing the curvature (or reducing the radius along at least a portion of the curvature) of the coronary sinus 300 that substantially encircles the Mitral valve annulus 302 thereby reshaping the Mitral valve or the Mitral valve annulus. Reshaping may also include decreasing the curvature (or increasing the radius along at least a portion of the curvature) of the coronary sinus 300 in a way that exerts pressure on the Mitral valve annulus 302 or the Mitral valve (not shown) and flattening a portion or a side of the Mitral valve annulus or the Mitral valve. Details of such a device can be found in the U.S. patent application Ser. No. 10/297,714 or No. 10/740,360. Of course, the device 320 can be other medical devices that have other functions (therapeutic and/or diagnostic).

Figure 6:
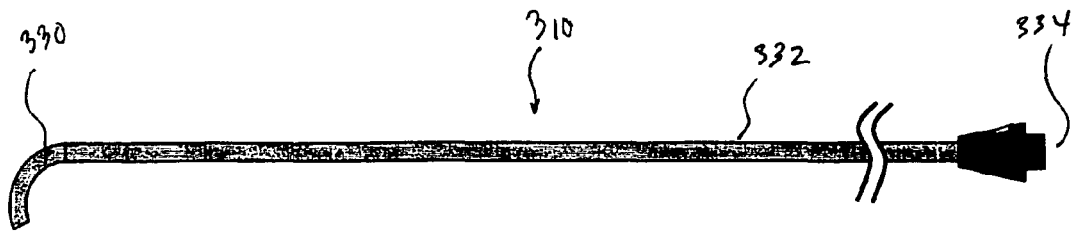
FIG. 6 illustrates an exemplary access guide catheter.

FIG. 6 illustrates an exemplary embodiment of an access guide catheter 310. In one embodiment, the access guide catheter 310 has the same basic shapes/lengths/design characteristics as the outer guide catheters currently designed to access the coronary sinus such as an 8 F (8-French) Easy Trak™ catheter system (Easy Trak is a trademark of Guidant Inc). In one embodiment, the access guide catheter 310 has the same basic shapes/lengths/design characteristics as guide catheters currently designed to access the coronary sinus via the superior or inferior vena cava. The access guide catheter 310 includes a curved section 330 to allow the access guide catheter 310 to easily access or sub-select a portion (e.g., a proximal portion) of the coronary sinus or the proximal portion of another vascular structure. The access guide catheter 310 includes a proximal support section 332 that may be stiffer than the curved section 330 to enable easy tracking of the access guide catheter 310 into the introducer sheath 310 and through the peripheral vasculature. The access guide catheter 310 may also include an access port 334 to allow for injection into the access guide catheter 310 or the connection of an RHV (Rotating Hemostasis Valve). The access port 334 is preferred to be a Luer configuration. The access guide catheter 310 may also include at least one lumen (not shown) that communicates with access port 334 and allows fluids injected (e.g., a contrast solution for visualization purposes) into the access port 334 to exit the distal end of the access guide catheter 310. This lumen may be configured sufficiently large for the rail catheter 312 to be inserted within it.

The inner diameter or outer diameter (ID/OD) of the access guide catheter 310 may be modified to accommodate the required OD of the rail catheter 312 and the delivery catheter 318. In one embodiment, the ID of the delivery catheter 318 and the access guide catheter 310 are preferred to be slightly greater than the OD of the rail catheter 312 to assure that the rail catheter 312 may move freely within them. The access guide catheter 310 is also designed to support the rail catheter 312 (FIGS. 8-9) during the rail catheter's initial access of the more distal portions of target vasculature, which can be the coronary sinus or other cardiac veins.

Figure 7:
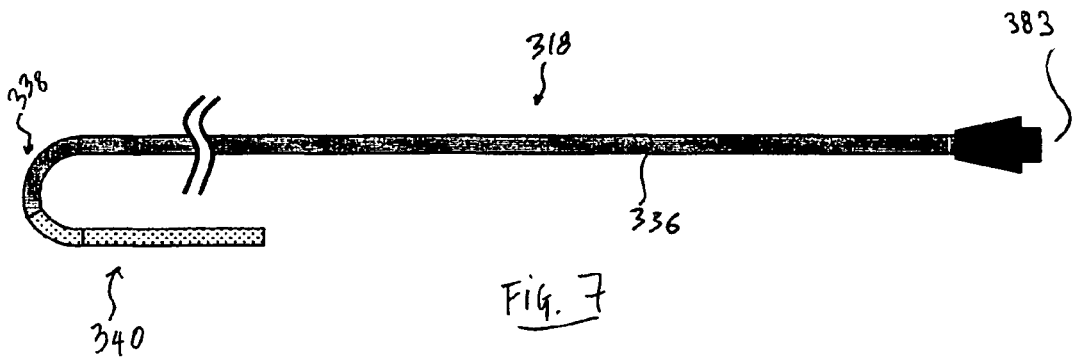
FIG. 7 illustrates an exemplary delivery catheter.

FIG. 7 illustrates an exemplary embodiment of a delivery catheter 318. In one embodiment, the delivery catheter 318 has a proximal portion 336 and a curved section 338 that is constructed/shaped in the same manner as normal guide catheters or the access guide catheter 310. In addition, the delivery catheter 318 has a flexible extension 340 (or a flexible distal portion). The delivery catheter 318 can be thought of as a normal guide catheter or as an access guide catheter with a flexible, pre-shaped, straight or bent extension, on its distal end. In one embodiment, the extension 340 is designed to easily conform to the shape of the target vasculature such as the shape of the coronary sinus and to follow the rail catheter's path. In one embodiment, the extension 340 is very flexible in comparison to the more proximal section 336 or the curved section 338 of the delivery catheter 318. The wall of the extension 340 may be made of a homogenous material, a material mix or miscible materials of differing flexibility. Additionally, the wall of the extension 340 may incorporate a low friction liner, have a varying wall thickness, and/or incorporate a coil or braid. In one embodiment, the extension 340 has as small an OD as practical. In one embodiment, the extension 340 has an ID that is similar to an ID of the proximal section 336 but the extension 340 may have an OD that is smaller than the OD of the proximal section 336. The extension 340 thus may have a smaller wall thickness that the wall thickness of the proximal section 336.

In one embodiment, the extension 340 has a length that is very close to the length between the distal portion or portions of the vasculature where the distal part of a device (e.g., the device 320) needs to be delivered to (e.g., a treatment site) (e.g., a portion of the coronary sinus or great cardiac vein) and the distal end of the access guide catheter 310 when it is in position in the vasculature. For illustration purposes, the extension 340 may have a length similar to the length L1 shown in FIG. 2. The length L1 is the portion between the portion where the distal part of the device 320 needs to be deployed and the portion where the access guide catheter 310 reaches in the coronary sinus. The proximal portion 336 and curved section 338 of the delivery catheter 318 may reside in a similar position relative to the target vasculature as the access guide catheter 310 after the delivery catheter 318 has replaced the access guide catheter 310. The delivery catheter 318 is longer than the access guide catheter 310 and has the same (or very close to the same) ID as the access guide catheter 310. The delivery catheter 318 provides a conduit for the device 320 as well as any catheter housing or incorporating the device 320 (e.g., the device delivery system/catheter) to reach the distal portion of the target vasculature while protecting the lumen walls of the target vasculature. The walls of the target vasculature are protected from direct contact with the device or device delivery system/catheter by the distal portions of the delivery catheter 318. The walls of the target vasculature are also protected from the concentrated deforming forces generated by the passage of the device or device delivery system/catheter. These forces are applied to the ID of the distal portions of the delivery catheter 318 (instead of directly to the lumen wall), which distributes the forces over the larger surface area of the OD and length of the distal portions of the delivery catheter 318 against the lumen wall. This distributed force is less than the concentrated force and results in less deformation of and damage to the lumen walls than if the concentrated forces where directly applied to the vessel wall.

In some embodiments, (e.g., when the delivery catheter is used for a pacing lead access/delivery system), the delivery catheter may be of a peel-away or cut-away design or configuration. In one embodiment, the delivery catheter has a single cut-away configuration, which can be helpful when used to deliver devices with large OD proximal portions into a coronary sinus such as the proximal electrical connector on a pacing lead. The peel away or cut-away design can be incorporated into the delivery catheter using methods well known in the art.

The delivery catheter 318 may also include an access port 383 to allow for injection (e.g., a contrast solution for visualization purpose) into the delivery catheter 318 and/or insertion of the device and its delivery system. Alternatively, a device, such as an RHV, may be attached to access port 383 to perform the same functions. The access port 383 is preferred to be a Luer configuration. The delivery catheter 318 may also include at least one lumen (not shown) configured for a device and/or its delivery system to be disposed therethrough and/or for the injection of fluids into the target vasculature out of the delivery catheter 318's distal end. The delivery catheter 318 may also be configured to deliver and/or deploy the implantable device into the target vasculature or the distal portion of the target vasculature.

Figure 8:
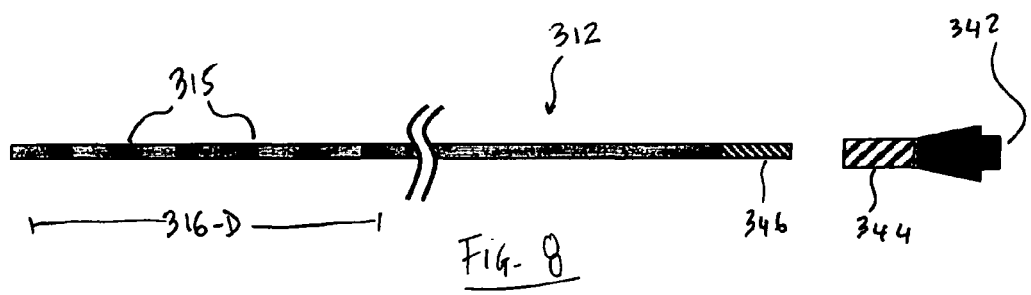
FIGS. 8-9 illustrate an exemplary rail catheter.
Figure 9:
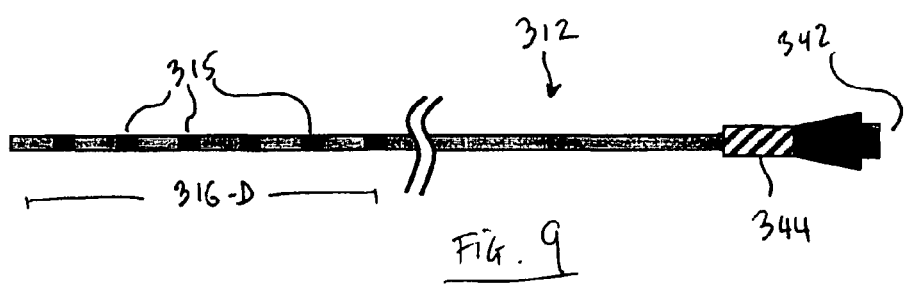

FIGS. 8-9 illustrate an exemplary embodiment of a rail catheter 312. The rail catheter 312 may be constructed with variable flexibility. In one embodiment, the rail catheter 312 is much longer than the access guide catheter 310 or the delivery catheter 318. In one embodiment, the rail catheter 312 is about twice as long as either the access guide catheter 310 or the delivery catheter 318 to assure that portions of the rail catheter 312 will be accessible to the physician to hold in place while the access guide catheter 310 is withdrawn or the delivery catheter 318 is inserted over the rail catheter 312. The rail catheter 312 may accommodate a guidewire in its ID and/or include a shaped distal end for easy maneuvering and sub-selection of the target vasculature. The rail catheter 312 includes an access port 342 that is detachable (FIG. 8 illustrates the access port 342 in its detached configuration and FIG. 9 illustrates the access port 342 in its attached position). The rail catheter 312 shown in FIGS. 8-9 have a detachable Luer as the detachable access port 342 which will allow the access guide catheter 310 to be removed over the rail catheter 312 and the delivery catheter 318 to be disposed over the rail catheter 312 without the access guide catheter 316 or the delivery catheter 318 having a very large ID. For a detachable access ports 342, the proximal end of the rail catheter 312 can be configured to include a male or female screw tip 346 that is complimentary with a respective male or female screw receptor on the distal tip on the access port 342. For example, as shown in FIG. 8, the rail catheter 312 includes a male screw tip 346 at the proximal end and the access port 342 includes a female receptor 344. The access port 342 is detached to allow the access guide catheter 310 to be withdrawn over the rail catheter 312 once the rail catheter 312 is in place. This way, the ID of the access guide catheter 310 and the OD of the rail catheter 312 can be substantially closer to each other. Additionally, the detachable access port 342 can be detached to allow the delivery catheter 318 to be tracked over the rail catheter 312. In this way, the ID of the delivery catheter 318 and the OD of the rail catheter 312 can also be substantially close to each other. For instance, the rail catheter 312 can have an OD that is about 0.002-0.010 inches smaller than the ID of the delivery catheter 318. The OD of the rail catheter and the ID of the delivery catheter should be substantially close to each other so they can move relatively easy with respect to each other without too much excess space between the OD of the rail catheter and the ID of the delivery catheter. In one embodiment, instead of a detachable Luer, the detachable access port 342 is an RHV (Rotating Hemostatic Valve) or other similar components.

A wide variety of commonly used attachment/detachment configurations can be used to facilitate the preferably water/blood tight access port attachment/detachment of the Luer (or other connection component) to the proximal end of the rail catheter 312. This engagement could be as simple as screw with an O-ring in the Luer (or other connection component) that mates with threads or a sealing surface on the proximal end of the rail catheter. Another simple engagement is to incorporate a conventional Touhy-Borst type of compression mechanism on the Luer (or other connection component) that compresses onto a sealing and/or retaining surface on the proximal end of the rail catheter 312. Such a surface could be as simple as a cut section of hypotube incorporated into the rail catheter's proximal end. Such a surface may also include texturing and/or a lip(s) to assist in retaining the Luer (or other component), once it is attached and under forces that would tend to remove it (e.g., during a contrast injection).

As shown in FIGS. 8-9, the rail catheter 312 includes a plurality of radiopaque markers 315 on the distal end 316-D. The markers 315 are placed at regular and/or known intervals along the distal end 316-D. Examples of radiopaque markers 315 materials include tungsten, gold, platinum and plastics filled with radiopaque powders, granules or filings of materials such as tungsten, bismuth compounds or barium compounds. The markers 315 are used to help the operator or physician to determine the length of the treatment area so that the device to be delivered can have its length configured accordingly. The distal section 316-D may also be constructed of a radiopaque material or comprise a radiopaque section for visualization purposes similar to currently employed in guiding catheters, angioplasty catheters, and stent delivery systems.

When contrast is injected into the rail catheter 312 (e.g., via the access port 342 or the sidearm of an RHV connected to its access port 342, with the rail catheter 312 resident inside the access guide catheter 310, and distal to it, the injected contrast will flow down and out of the rail catheter 312. This provides a way for injecting contrast distally in the veins or vessels to aid in visualization of the veins or vessels or the target vasculature as the rail catheter 312 is guided into position. When contrast is injected, the outline of the anatomy of the target vasculature can be visualized using fluoroscopy. The location of the treatment area can be determined or ascertained. Other properties of the treatment area (e.g., the diameters of the treatment area) can be determined or ascertained. In addition, with the presence of the markers 315 on the rail catheter 312, the length (or treatment length) of the treatment site within the target vasculature can be measured based on the known intervals of the markers 315. Alternatively or in addition, the guidewire used in conjunction with the rail catheter 312 may contain such markers. In some cases, the required measurements may be aided by visualizing other relevant anatomy using other catheters, injections or guidewires in the adjacent anatomy or vasculature (for example, contrast injections into the left ventricle, a radiopaque catheter or guidewire resident in the circumflex coronary artery). The ability to determine lengths and/or diameters of the treatment site and their relationship to adjacent vessels and other cardiac structures within the target vasculature or adjacent to the target vasculature allows one to select the delivery catheter 318 and the medical device with proper sizes and select their desired placement locations. For instance, it is likely very desirable that the distal end of the delivery catheter 318 be more flexible than its proximal/support portions. Alternatively or in addition, it may be very desirable that a curved or shaped and less flexible section of the rail catheter 312 be located between the distal and proximal sections of the delivery catheter 318 when the rail catheter is in its most distal position. It is also likely that the OD of the distal end of the delivery catheter 318 will be too large to go very distal into the coronary sinus or other cardiac veins. Thus, to assure that the interface between the more flexible distal portion of the delivery catheter 318 and its more supportive proximal portions is located properly (e.g., near the entrance to the coronary sinus) and that the delivery catheter 318 may be inserted such that its distal end is properly placed (e.g., at, near, or distal to the desired position of the distal end of the device or device delivery system/catheter), a delivery catheter 318 with the proper length of flexible distal end may need to be selected.

Figure 10:
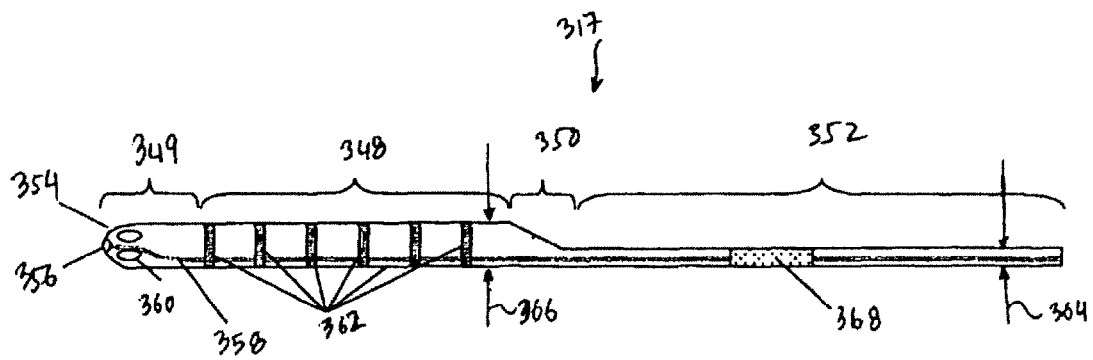
FIGS. 10-11 illustrate another exemplary rail catheter.
Figure 11:
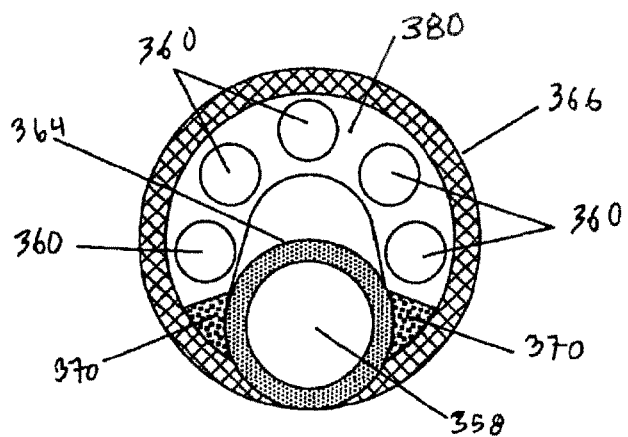

FIGS. 10-11 illustrate another exemplary embodiment of a rail catheter 317. The rail catheter 317 can be used in place of the rail catheter 312 throughout embodiments of the present invention. In one embodiment, the rail catheter 317 includes four sections, a distal tip section 349, a distal body section 348, a transition section 350, and a proximal section 352. The rail catheter 317 may be constructed with variable flexibility. In one embodiment, the rail catheter 317 is much longer than either the access guide catheter 310 or the delivery catheter 318 (e.g., at least twice as long). The rail catheter 317 may accommodate a guidewire. This guidewire accommodation can be easily designed to be a rapid exchange type or other type of suitable engagement, such as an over the wire engagement. A lumen can also be provided in the rail catheter 317 to accommodate the guidewire.

The distal tip section 349 is flexible and bendable. The distal tip section 349 may be bent or curved (not shown) for easy maneuvering and vessel sub-selection. In one embodiment, the OD of the distal tip section 349 may be the same or smaller than that of the distal body section 348. The distal end of this section 349 has a rounded atraumatic tip 354. Alternatively, the distal end of section 349 may be a tapered/soft tip (not shown), such as those employed on angioplasty catheters or simply a blunt soft tip (not shown), such as those employed on guide catheters. In one embodiment, the distal tip section 349 or at least the tip 354 is radiopaque to allow the location of the distal end of the rail catheter 317 to be visualized by fluoroscopy.

The tip 354 also includes a guidewire exit port 356 which may be an exit of a guidewire lumen 358 that may run the entire length of the rail catheter 317. The guidewire lumen 358 may be lined with or its inner diameter is constructed with a low friction material for part or all of its length. The guidewire exit port 356 is preferably located at or near the center of the tip 354. It is preferred that the atraumatic tip 354 includes a contrast exit port or ports 360 that communicate with a separate internal lumen of the distal tip section 349, distal body section 348 and the transition section 350. In the embodiment where the distal end of the section 349 is a blunt soft tip (not shown), the guidewire lumen 358, the guidewire exit port 356 and the contrast exit port or ports 360 may not be required. Instead, if used, a guidewire may engage the rail catheter 317 through the central lumen 380 of the transition section 350, the distal body section 348 and the distal tip section 349. This would be one example of an RX guidewire engagement. In another embodiment, the guidewire lumen 358 need not extend the entire length of the rail catheter 317. The rail catheter 317 may include another exit port (not shown) proximal of the distal body section 348 or the transition section 350 and no guidewire lumen 358 would be required proximal of this new exit port (not shown). This would be another example of an RX guidewire engagement design.

Continuing with FIGS. 10-11, and with reference to FIGS. 2-5, in one embodiment, the distal body section 348 is a tube that incorporates a central lumen 380 and a separate guidewire lumen 358. The OD of the distal body section 348 is configured to be closely and slidably fitted within the ID of the access guide catheter 310 and the delivery catheter 318. In one embodiment, the OD of the distal body section 348 is substantially the same as the OD of a medical device 320 (or the device delivery system/catheter) so that the delivery catheter 318 can slidably accommodate the device 320 (or device delivery system/catheter) in the ID of the delivery catheter 318 (after the rail catheter 317 is withdrawn). The length of the distal body section 348 is chosen such that when the rail catheter 317 is in its most distal position in the target vasculature and in its most distal position relative to the access guide catheter 310, at least a small proximal length of the distal body section 348 will still be resident inside the access guide catheter 310. In one embodiment, the outer wall of the distal body section 348 includes a braid or coil(s) for reinforcement or support.

In one embodiment, the rail catheter 317 includes a plurality of markers such as radiopaque markers 362 placed along the distal body section 348 at regular and/or known intervals along its length. The makers 362 provide the same functions as the markers 315 previously described for the rail catheter 312. The proximal section 352 may or may not include similar radiopaque markers. The radiopaque markers 362 may be marker bands (metallic band/wires or filled plastic) or alternating sections of differently filled (different radiopacity) plastic (jacket) material. Examples of radiopaque materials include tungsten, gold, platinum and plastics filled with radiopaque powders, granules or fillings of materials such as tungsten, bismuth compounds or barium compounds. The distal body section 348 may also be constructed of a radiopaque material for visualization purposes similar to those currently employed in guiding catheters, angioplasty catheters, and stent delivery systems.

When contrast is injected into the access guide catheter 310, with the rail catheter 317 resident inside the access guide catheter 310, and distal to it, the bulk of the injected contrast will flow down the central lumen of the transition section 350 and the distal body section 348, down the internal lumen of the distal tip section 349 and out the contrast exit port or ports 360. This provides a way for injecting contrast distally in the veins or vessels to aid in visualization of the veins or vessels or the target vasculature as the rail catheter 317 is guided into position. When contrast is injected, the outline of the anatomy of the target vasculature can be visualized using fluoroscopy. The location of the treatment area can be determined or ascertained. Other properties of the treatment area (e.g., diameters) can be determined or ascertained. In addition, with the presence of the markers 362 on the rail catheter 317, the length (or treatment length) of the treatment site within the target vasculature can be measured based on the known intervals of the markers 362. In some cases, the required measurements may be aided by visualizing other relevant anatomy using other catheters and injections in the adjacent anatomy or vasculature (for example, contrast injections into the left ventricle, a catheter resident in the circumflex coronary artery). The ability to determine the length and/or diameters of the treatment site within the target vasculature or adjacent to the target vasculature allows one to select the delivery catheter 318 and the device 320 with proper sizes. For instance, it is likely very desirable that the distal end of the delivery catheter 318 (portion to be resident in the target vasculature at the treatment site, the extension 340) be more flexible than its proximal/support portions (338 and 336) (see FIG. 7). Alternatively or in addition, it may be very desirable that a curved or shaped and less flexible section 338 be located between the distal and proximal sections of the delivery catheter 318. It is also likely that the OD of the distal end of the delivery catheter 318 will be too large to go very distal into the coronary sinus or other cardiac veins. Thus, to assure that the interface between the more flexible distal portion of the delivery catheter 318 and its more supportive proximal portion (336) is located properly (e.g., near the entrance to the coronary sinus) and that the delivery catheter 318 may be inserted such that its distal end is properly placed (e.g., at, near, or distal to the desired position of the distal end of the device or device delivery system/catheter), a delivery catheter 318 with the proper length of flexible distal end may need to be selected.

In one embodiment, the length of the distal body section 348 is chosen such that the transition section 350 and the proximal section 352 will not be resident in the target vasculature's treatment site when the access guide catheter 310 is withdrawn and the delivery catheter 318 is advanced over the rail catheter 317.

In one embodiment, the transition section 350 provides a transition from the proximal section 352 to the distal body section 348 of the rail catheter 317. The transition section 350 provides the proximal section 352, which may have a small OD 364 to transition to the distal body section 348, which has a larger OD 366. With the transition section 350, when the delivery catheter 318 is advanced over the rail catheter 317, the distal tip of the delivery catheter 318 will not hang up/get caught on the OD transition. In one embodiment, the transition section 350 is beveled so that the delivery catheter 318 can be easily advanced over the rail catheter 317.

Still with FIGS. 10-11, in one embodiment, the proximal section 352 is the longest section of the rail catheter 317 and encloses the guidewire lumen 358. The proximal section 352 may also have a reinforced wall. The OD of the proximal section is smaller to allow contrast to flow between its OD and the ID of the access guide catheter 310 or the ID of the delivery catheter 318.

The proximal section 352 may contain a special resilient and/or higher friction section 368 that may be compressed by a clip or other pinching device to hold a guidewire in a fixed position relative to the rail catheter 312 when the access guide catheter 310 is being withdrawn or the delivery catheter 318 is being moved over the rail catheter 312. In one embodiment, a clip of a pinching device (not shown) is placed over the section 368 on the OD of the rail catheter 317 to hold the guidewire in place within the rail catheter 317. This clip or pinching device would have beveled ends and an OD that is smaller than the ID's of the access guide catheter 310 and the delivery catheter 318 to facilitate the movement of the access guide catheter 310 and the delivery catheter 318 over the clip. In one embodiment, the position of the section 368 is preferred to be just proximal of the access guide catheter 310 (or the RHV connected to it) or the delivery catheter 318 (or the RHV connected to it) when the rail catheter 317 is in its most distal position relative to them.

In many embodiments, it is preferred that the guidewire, if used, be completely removed from the rail catheter after the rail catheter is in its desired distal position (see for example, FIGS. 3-4, the guidewire 314 is removed after the rail catheter 312 is in place as previously discussed). This eliminates the necessity of holding or clamping the guidewire in place relative to the rail catheter during access guide catheter withdrawal and delivery catheter insertion. When the guidewire is present in the rail catheter during access guide catheter withdrawal and is not held in position, the ID of the access guide catheter may drag on the proximal end of the guidewire and cause the guidewire to move proximally, potentially removing the guidewire from the rail catheter. When the guidewire is present in the rail catheter during delivery catheter insertion and is not held in position, the ID of the delivery catheter may drag over the proximal end of the guidewire and cause it to move distally into the anatomy, which may cause damage or perforation to vessels or other cardiac structures. In addition, if the guidewire is used and not removed after the rail catheter has attained its desired distal position or during delivery catheter insertion, in some embodiments, (such as those shown in FIGS. 8-9), the guidewire would have to be very long (longer than three times the access guide catheter length) to always provide an exposed length to hold on to during system use and would likely require a separate person just to manage the guidewire. The rail catheter 317 configuration shown in FIGS. 10-11 has an optional frictional section 368 for clamping the guidewire into position (so the guidewire can be much shorter (longer than the rail catheter)), in the case where the user prefers to leave the guidewire in the rail catheter or the rail catheter is designed to require the support of the guidewire during access guide catheter withdrawal and/or delivery catheter insertion.

FIG. 11 is a representation of what an exemplary rail catheter 317 looks like when viewed from its proximal end and down its long axis. The OD of the transition section 350 and distal body section 348 is labeled 366. The OD of the proximal section 352 is labeled 364. In one embodiment, filling materials 370 (e.g., jacket, adhesive, etc. . . . ) are included to hold the tubing or material construction that forms the guidewire lumen 358 to the ID of the distal body section 348. Some of the contrast exit ports 360 may not be visible as they may be covered from view by the guidewire lumen 358 as it rises up to position the guidewire exit port 356 (not visible in this view) near the center of the tip 354.

As can be seen, by using the access guide catheter and the rail catheter to support the initial access of the target vasculature (e.g., the coronary sinus) and sub-select the distal portions of the target vasculature where the treatment site is (e.g., great cardiac vein and other veins communicating with the coronary sinus) and then maintaining this access with the delivery catheter after the access guide catheter and the rail catheter are removed, a device or catheter can be delivered to the treatment site with better device design and optimization. Since one catheter or device replaces the other, the size of the access guide catheter, the rail catheter, the delivery catheter, the device and the catheter that houses or incorporates the device can be minimized. Also the sizes of the device and/or the catheter incorporating or housing the device are further minimized because no guidewire is required to deliver the device or the catheter housing the device to the treatment site.

It is noted here that besides the rail catheters, the access guide catheter and the delivery catheter may also include similar radiopaque markers and/or sections for similar functions as previously described. The radiopaque markers or radiopaque sections may be made in manners currently employed in guiding catheters, angioplasty catheters and stent delivery systems. Additionally, the constructions of the access guide catheters, the delivery catheters, and the rail catheters previously described can be constructed similarly to conventional guide catheter construction.

Contrast may be injected into the access guide catheter or rail catheter to fill the coronary sinus and communicating vasculature (or other target vasculatures) with the contrast so that the coronary sinus and the communicating vasculature (or other target vasculatures) may be visualized by fluoroscopy to aid in the positioning of the guidewire (if used), the access guide catheter and the rail catheter. Sidearms of RHV's connected to the proximal ports (Luers) of these catheters may be used for the contrast injection, if desired, but on the venous side, the pressures are low enough that they may not be required in some embodiments, if the fits are close enough and sidearms are provided on the appropriate access ports.

Figure 12:
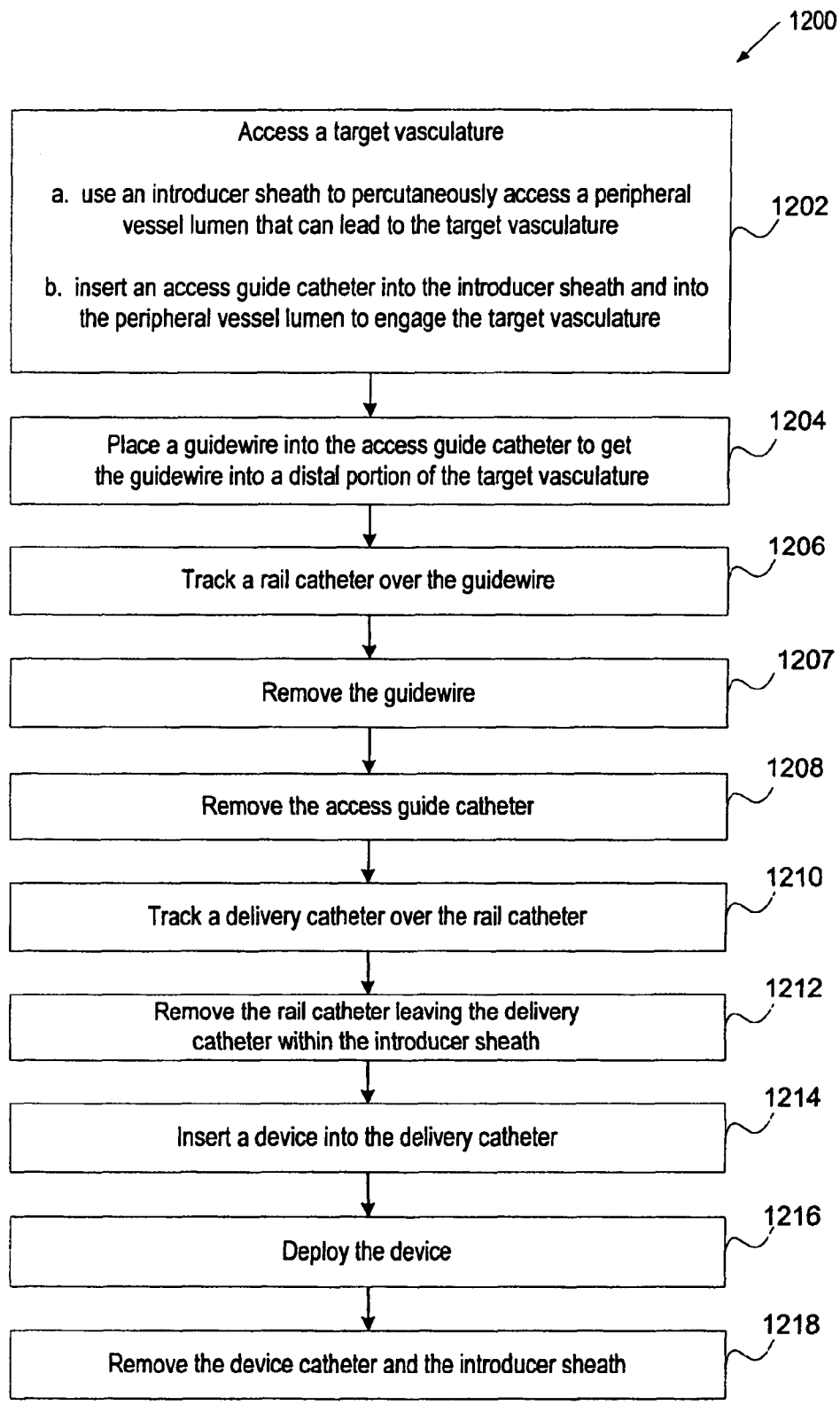
FIG. 12 illustrates another method of delivering a device into a target vasculature in accordance to embodiments of the present invention.
Figure 15A:
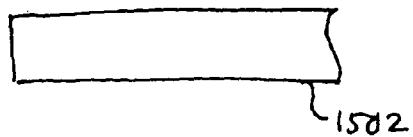
FIGS. 15A-15J illustrate various components of a delivery system in accordance to embodiments of the present invention at various stages of delivering.
Figure 15B:
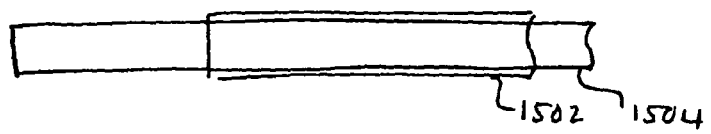
Figure 15C:
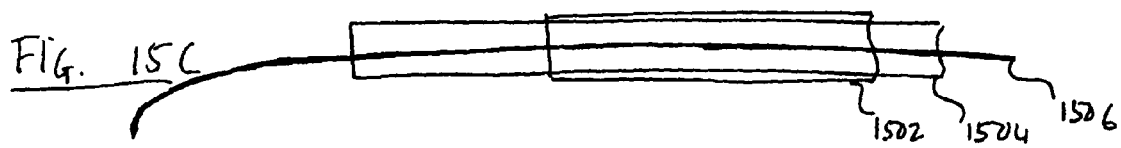

Various methods can be used to access a target vasculature, sub-select distal portions of the target vasculature, and deliver a device using the components described. FIG. 12 illustrates an exemplary embodiment (method 1200) of delivering a device (e.g., a Mitral valve repair device) into a target vasculature and the target vasculature's distal portion (e.g., great cardiac vein). FIGS. 15A-15J accompany the method 1200 to illustrate the various components of the delivery system employed in the method 1200 at various stages of the delivering process. At box 1202, a percutaneous access is made to a vessel lumen (not shown) that can lead to the target vasculature (not shown) using an introducer sheath 1502 (FIG. 15A). An access guide catheter 1504 is then inserted into the introducer sheath 1502 to sub-select the target vasculature (FIG. 15B). Many of the embodiments discuss delivering and accessing the coronary sinus and the great cardiac vein, but it is to be understood that the embodiments are similarly applicable to other target vasculature structures such as blood vessels, arteries, or veins located in other parts of the body or vascular structures like the chambers of the heart. In one embodiment, the target vasculature is the coronary sinus and in this embodiment, the access guide catheter is inserted percutaneously through the introducer sheath into a peripheral vessel lumen to access and engage the entrance of the coronary sinus. The access guide catheter 1504 is placed at a proximal portion of the target vasculature.

At box 1204, a guidewire 1506 is placed into the access guide catheter 1504 and into a distal portion of the target vasculature (FIG. 15C) such as the great cardiac vein (not shown). The guidewire 1506 thus sub-selects the distal portion of the target vasculature. The guidewire 1506 is placed distally to the access guide catheter 1504 and the access guide catheter 1504 is placed distally to the distal end of the introducer sheath. In one embodiment, the distal portion of the target vasculature is the treatment site or site of interest where a device needs to be placed.

Figure 15D:
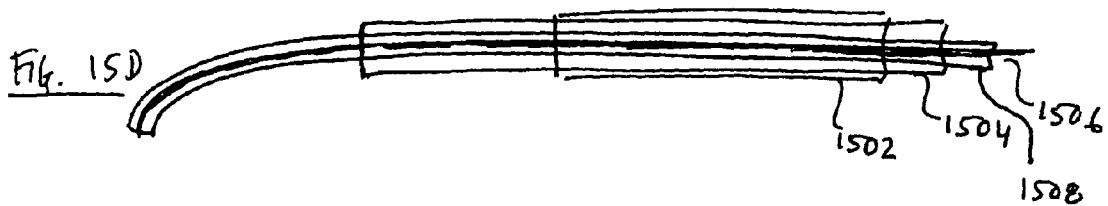
Figure 15E:
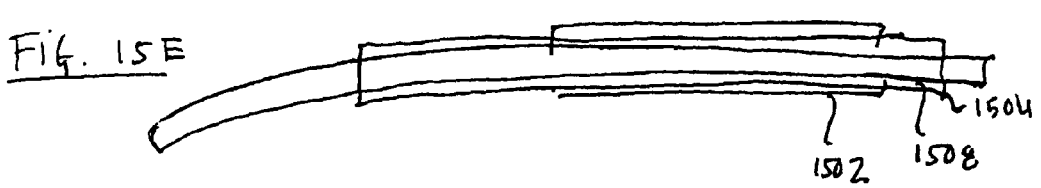
Figure 15F:
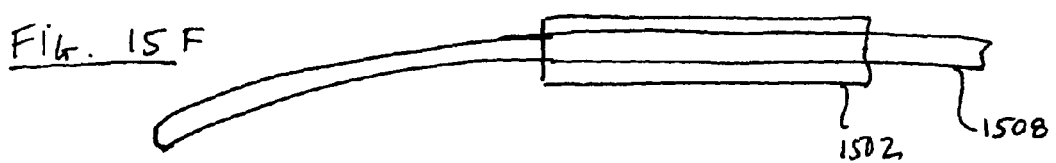
Figure 15G:
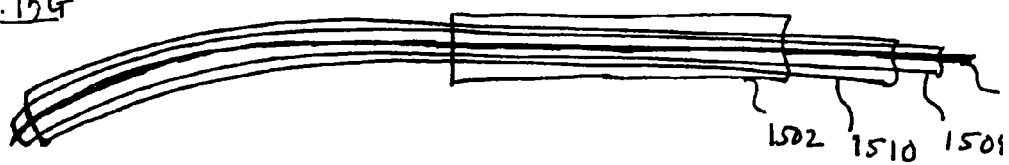
Figure 15H:
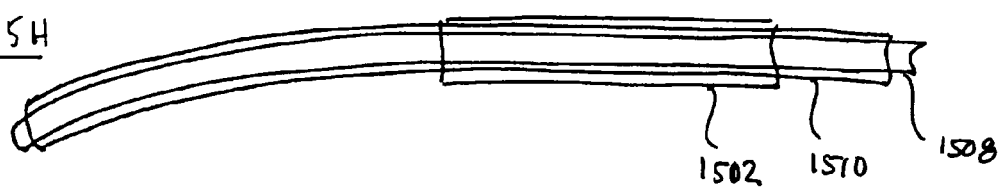
Figure 15I:
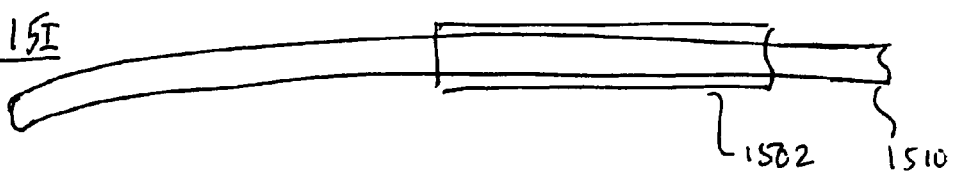

Still with FIG. 12, at box 1206, a rail catheter 1508 is tracked over the guidewire 1506 and within the access guide catheter 1504 and the introducer sheath 1502 (FIG. 15D). It should be noted that in some embodiments, the use of the guidewire 1506 may be omitted and the rail catheter 1508 used exclusively to gain the distal access or, if the rail catheter 1508 fails to gain the desired distal access, the guidewire 1506 may then be inserted into the proximal end of the rail catheter 1508 and out its distal end to gain the desired distal access. The rail catheter 1508 is placed distally to the access guide catheter 1504 and into the distal portion of the target vasculature. At box 1207, the guidewire 1506 is removed (FIG. 15E). It should be noted that when a rail catheter has a configuration similar to that described with reference to FIGS. 10-11 where the rail catheter has a friction section that can clamp the guidewire into position, the guidewire needs not be removed after the rail catheter is in place as previously described (FIG. 15G). At box 1208, the access guide catheter 1504 is removed leaving the rail catheter 1508 within the introducer sheath 1502 and extending distally and proximally therefrom (FIG. 15F). The rail catheter 1508 extends proximally to the introducer sheath 1502 to provide the operator or the physician the necessary access to the rail catheter 1508. At box 1210, a delivery catheter 1510 is tracked over the rail catheter 1508 and within the introducer sheath 1502 into the distal portion of the target vasculature (e.g., the great cardiac vein) (FIG. 15H). In the embodiment where the guidewire needs not be removed as previously mentioned, the delivery catheter 1510 is tracked over the rail catheter 1508 that has within it the guidewire 1506 as shown in FIG. 15G. At box 1212, the rail catheter 1508 is removed leaving the delivery catheter 1510 within the introducer sheath 1502 and also extending proximally therefrom (FIG. 15I). At this point, if the guidewire has not been removed as mentioned for some embodiments, the guidewire is also removed.

Figure 15J:

At box 1214, a medical/diagnostic device 1512 is inserted into the delivery catheter 1510 (FIG. 15J). The device 1512 may be included in its own device catheter and thus, the device catheter plus the device itself are inserted together into the delivery catheter 1510. It may be that the delivery catheter 1510 and the device are configured so that there is no need for the device catheter in order for the device to be inserted into the delivery catheter 1510 and delivered. For example, a diagnostic camera or a pacing lead typically could be inserted into a patient through a tube similar to the delivery catheter 1510 without the need to be packaged in a special device catheter. The device 1512 is positioned at the treatment or diagnostic location within the delivery catheter 1510.

At box 1216, the device is deployed or delivered within target vasculature and in one embodiment, within the great cardiac vein. In one embodiment, to deploy the device, the delivery catheter is retracted proximally while the device (or the device catheter that incorporates or houses the device) is held in place to allow the device to be exposed to the target vasculature prior to its being deployed (or for some devices, like pacing leads, exposure to the vasculature may constitute deployment). The device may also need to be retracted or re-positioned to a more optimal position within the target vasculature to deploy the device. Some medical devices may have more than one component to be deployed. In such event, the delivery catheter and/or device or catheter incorporating or housing the device may be further retracted to allow the deployment of a more proximal portion or components of the device into the target vasculature. It is to be understood that retracting the delivery catheter is not the only way to or does not necessarily deploy certain devices. For example, it is common for a device to be deployed by inflating a balloon, withdrawing an outer member, screwing or unscrewing a threaded attachment, withdrawing a cord, etc., either in or on the device or on the catheter that houses or incorporates the device. If the device is a pacing lead, it is common that retracting the delivery catheter deploys the lead's electrode (allows the electrode to pace the adjacent heart muscle). At box 1218, the delivery catheter 1510 and the introducer sheath 1502 are removed after the device 1512 is completely deployed. In the embodiments where the device 1512 is housed in its own device catheter, the device catheter may be removed prior to the removal of the delivery catheter 1510 and the introducer sheath 1502. As with other embodiments, the device can be a Mitral valve repair system previously disclosed (e.g., a Mitral valve repair device disclosed in U.S. patent application Ser. No. 10/297,714 and No. 10/740,360 previously mentioned).

It is to be noted that the contrast may be injected into the rail catheter or the access guide catheter as previously discussed. In embodiments where the rail catheter has a configuration like that shown in FIGS. 8-9 (the rail catheter 312), then the contrast is preferred to be injected into the rail catheter via its access port or an RHV connected to its access port. The rail catheter 312 tends to have an OD that is a close fit to the ID of the rail catheter. If the contrast were attempted to be injected into the access guide catheter, the close fit of the OD of this rail catheter to the ID of the access guide catheter may make getting significant contrast to flow out of the distal end of the access guide catheter difficult (due to the very constricted/small flow channel). For this rail catheter 312 configuration, it is preferred that the guidewire chosen/designed to be inserted into the rail catheter 312 have an OD small enough relative to the ID of the rail catheter 312 that there is a sufficient flow channel between them for significant contrast flow (or the guidewire must be withdrawn prior to contrast injection). And, it is preferred that the contrast be injected into the rail catheter.

In the embodiments where the rail catheter has a configuration similar to the rail catheter 317 described with reference to FIGS. 10-11, the contrast is preferred to be injected into the access guide catheter via its sidearm access port (if included) or via the sidearm of an RHV connected to the access port. In this rail catheter 317 configuration, there is plenty of room between the proximal OD 364 of this rail catheter 317 and the ID of the access guide catheter for significant contrast flow. At the distal end of the access guide catheter, the OD 366 of the more distal end 350, 348 of the rail catheter 317 is a close fit to the ID of the access guide catheter, so little contrast flows down this small channel and out the distal end of the access guide catheter. However, as shown/described, this distal end 350, 348 of the rail catheter 317 has an ID that is open and relatively large at this point, so significant contrast flow is directed down this ID of the rail catheter 317 and out its distal end via port or ports 360. It is preferred to have significant contrast flow out of the most distal catheter exit into the venous vasculature to visualize the more distal regions of the venous vasculature to guide the placement of the guidewire and/or the rail catheter and/or make measurements.

In many embodiments during the insertion procedure, the access guide catheter does not always have the most distal exit. In a particular rail catheter configuration with the preferred contrast input location as previously described (e.g., through the rail catheter or through the access guide catheter), if the distal end of the rail catheter is proximal to the distal end of the access guide catheter, then the significant contrast flow out of the distal end of the rail catheter will empty out into the ID of the access guide catheter and flow out the distal end of the access guide catheter (which is the most distal exit). In another particular rail catheter configuration with the preferred contrast input location as previously described (e.g., through the rail catheter or through the access guide catheter), if the rail catheter is distal to the access guide, then the significant contrast flow will be out of the distal end of the rail catheter (which is the most distal exit).

The close fit of the OD of the rail catheter to the ID's of the access guide catheter and the delivery catheter is preferred because this allows the system components to be designed with the minimum OD's (minimizes insertion site complications/allows the system to attain more distal access or to access smaller vessels).

Figure 13:
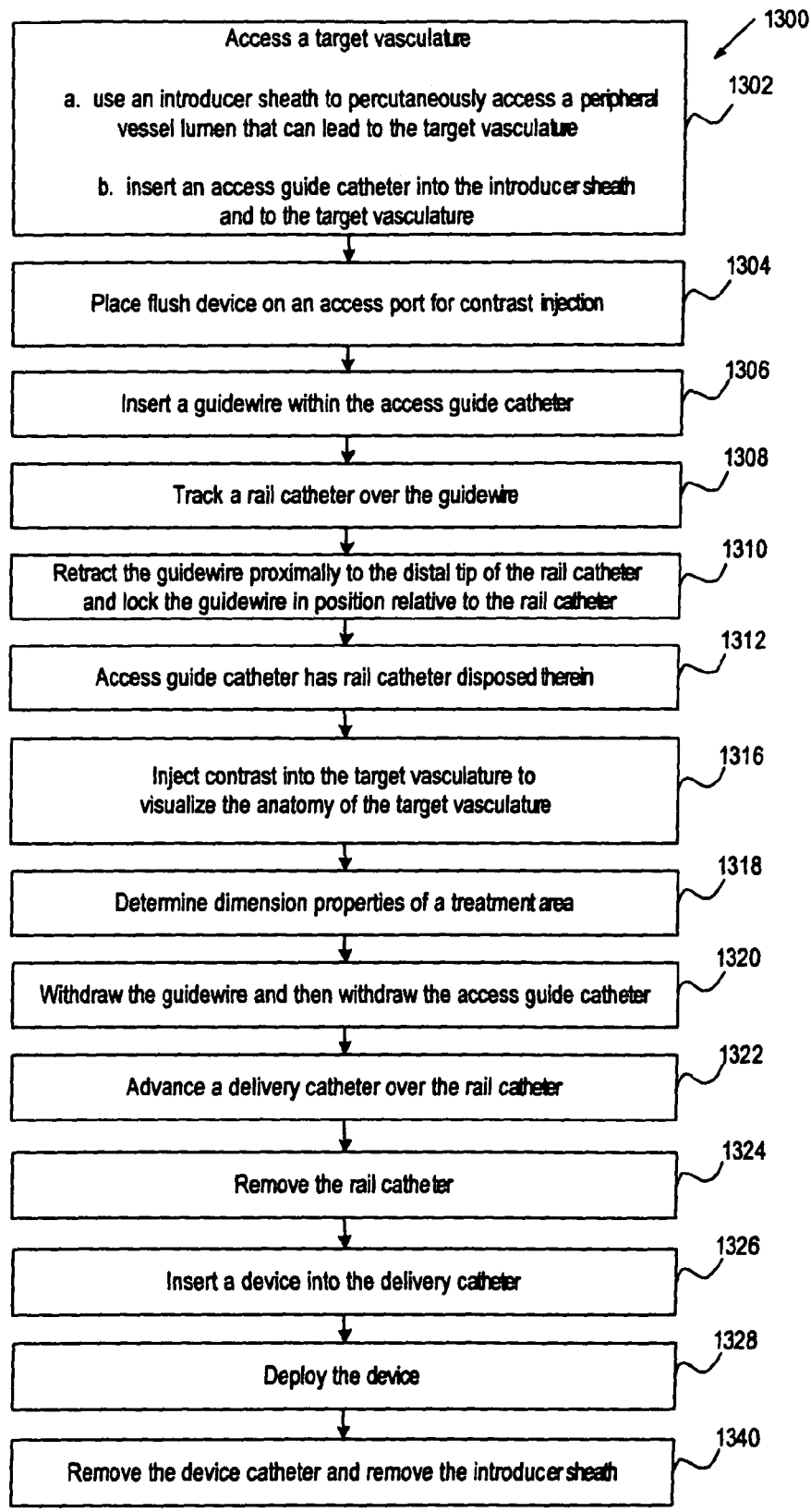
FIG. 13 illustrates another method of delivering a device into a target vasculature in accordance to embodiments of the present invention.

FIG. 13 illustrates another exemplary embodiment (method 1300) of delivering a device (e.g., a Mitral valve repair device) into a target vasculature (e.g., the great cardiac vein). The method 1300 is similar to the method 1200 with the addition of adding a flush device, an access port, and using contrast solution. The illustrations of the components shown in FIGS. 15A-15J are similarly applicable to the method 1300. The method 1300 is discussed in relation to delivering the device across the coronary sinus and into the great cardiac vein, but as previously discussed, the target vasculature and the treatment site can be in other vessels and vascular structures in other parts of the body. At box 1302, a percutaneous access is made to a peripheral vessel lumen that can lead to the target vasculature. In one embodiment, access is made percutaneously into the entrance of a coronary sinus. In one embodiment an introducer sheath is used to percutaneously access a peripheral vessel and the access guide catheter is inserted into the introducer sheath to engage the coronary sinus at the entrance of the coronary sinus.

Continuing with FIGS. 13, at box 1304, a sidearm or flush device (e.g., an RHV, with a closed stopcock on its sidearm/flush Luer) is placed on the access port of the access guide catheter for contrast injection as previously described. In one embodiment, the sidearm may be a part of the access port (Luer) provided on the proximal end of the access guide catheter. The contrast may be injected through the rail catheter or the access guide catheter as previously described. At box 1306, a guidewire is placed into the access guide catheter (through the RHV, in one embodiment) to allow the guidewire to access a distal portion of the target vasculature. In the embodiments where the target vasculature is the coronary sinus, the distal portion of the target vasculature may include a portion of the great cardiac vein. The access guide catheter is placed distally to the introducer sheath and the guidewire is placed distally to the access guide catheter. In an alternative embodiment, the guidewire is placed inside the access guide catheter prior to the introduction of the access guide catheter into the introducer sheath.

Still with FIG. 13, at box 1308, a rail catheter is tracked over the guidewire and within the access guide catheter and the introducer sheath. At box 1310, the guidewire is retracted just proximally to the distal tip of the rail catheter. The guidewire is then locked in position relative to the rail catheter. In one embodiment, the rail catheter is configured so that it can be maneuvered (e.g., via rotation, retraction and/or advancement) to sub-select the treatment site within the distal portion of the coronary sinus (e.g., great cardiac vein). When rotation and retraction and/or advancement of the rail catheter is not sufficient to sub-select the treatment site within the coronary sinus or other vessels, the guidewire is unlocked, manipulated to select/advance into the treatment site within the coronary sinus or other vessels. Then, the rail catheter is advanced over the guidewire to attain the desired more distal position in the vasculature. As before, in some embodiments, the use of the guidewire may be omitted and the rail catheter used exclusively to gain the distal access or, if the rail catheter fails to gain the desired distal access, the guidewire may then be inserted into the proximal end of the rail catheter and out its distal end to gain the desired distal access. Box 1312 shows that at this point, the access guide catheter has the rail catheter disposed therein.

At box 1316, a contrast solution is injected into the access guide catheter to visualize the target vasculature to allow for visualization of the anatomy of the target vasculature (e.g., the coronary sinus). The contrast solution may be injected through the rail catheter or the access guide catheter as previously described. The contrast injection allows fluoroscopic visualization of the distal vasculature to facilitate the guidance of the guidewire and/or rail catheter to the desired position in the target vasculature. Once the injected contrast has washed out, the radiopaque portions of the guidewire, access guide catheter and the rail catheter may be visualized under fluoroscopy. Other catheters or guidewires in other vessels or vascular structures or other contrast injections may also be visualized by fluoroscopy to help further identify and measure the treatment area. At box 1318, dimension properties such as the length and/or diameter of the treatment area are determined to enable one to select a device with an appropriate size/length. In one embodiment, the rail catheter includes a plurality of radiopaque markers that can be visualized under fluoroscopy. With the contrast injected and/or with the visualization of other catheters, the anatomy of the target vasculature e.g., the coronary sinus, the great cardiac vein and other relevant anatomy, and the length of the treatment area can be determined. As previously mentioned, the radiopaque markers being spaced at regular and/or known intervals allow for the length determination of the treatment area.

At box 1320, the guidewire is removed and then the access guide catheter is removed proximally and over the OD of the rail catheter, leaving the rail catheter within the target vasculature. At box 1322, a delivery catheter configured to deliver a medical/diagnostic device is tracked over the rail catheter (and within the introducer sheath) and into the target vasculature and the distal portion of the target vasculature. At box 1324, when the delivery catheter is in the desired position (e.g., over the distal portion of the rail catheter, in the target vasculature distal portion or within an appropriate location in the great cardiac vein, coronary sinus or other communicating vasculature structure), the rail catheter is removed leaving the delivery catheter within the target vasculature.

At box 1326, the medical/diagnostic device is inserted into the delivery catheter. The device may be delivered together with its own device catheter as previous discussed. In such embodiments, the device catheter plus the device are both inserted within the delivery catheter. At box 1328, the device is deployed and in one embodiment, deployed within the great cardiac vein. In one embodiment, to deploy the device, the delivery catheter is retracted proximally while device is held in place to allow the device to be exposed to the vasculature. For some medical/diagnostic devices, exposure of the device is all that is necessary to deploy the device (e.g., as in the case when the device is a pacing lead). The delivery catheter may be further retracted to expose more proximal portions of the device and allow completion of the deployment. In embodiments where the device is included in its own device catheter, the device catheter may also need to be withdrawn to place the device in the optimum position to be deployed.

In one embodiment, the device is a Mitral valve repair system including a distal anchoring member and a proximal anchoring member connected by a telescoping assembly as previously disclosed. A cord is included in the Mitral valve repair system to lock the system in place. The Mitral valve repair system is typically housed in its own device catheter and thus is inserted within the delivery catheter together with the device catheter. In the embodiment where the device is a Mitral valve repair system, the delivery catheter is withdrawn proximally in order to expose the Mitral valve repair system to the vasculature. The distal anchoring member is then deployed by expanding such that the distal anchoring member contacts the inner wall of the target vasculature. Once the distal anchoring member is deployed, the delivery catheter and the device catheter are withdrawn more proximally (e.g., to the ostium of the coronary sinus). The position of the proximal anchoring member is adjusted by moving the delivery system of the device. The proximal anchoring member is deployed in a similar manner as that described for the distal anchoring member, and in one embodiment, at the entrance of the coronary sinus. The telescoping member is then adjusted to provide the cinching of the Mitral valve annulus to reverse Mitral valve regurgitation. The cord is then locked to make the telescope adjustment be retained. A pull loop may be included so that pulling on the cord (via another loop at the proximal end of the cord) to make this adjustment. The pull loop is broken and is withdrawn from contact with the loop of the cord when the Mitral valve repair system is locked in place. With this loop material (a thread or other thin line) withdrawn, the device is freed from its delivery system and the device is fully deployed. The delivery system may then be withdrawn from the delivery catheter, leaving the deployed device in the vasculature. At box 1340, after the device is deployed, the delivery catheter and then the introducer sheath are withdrawn completely.

Figure 14:
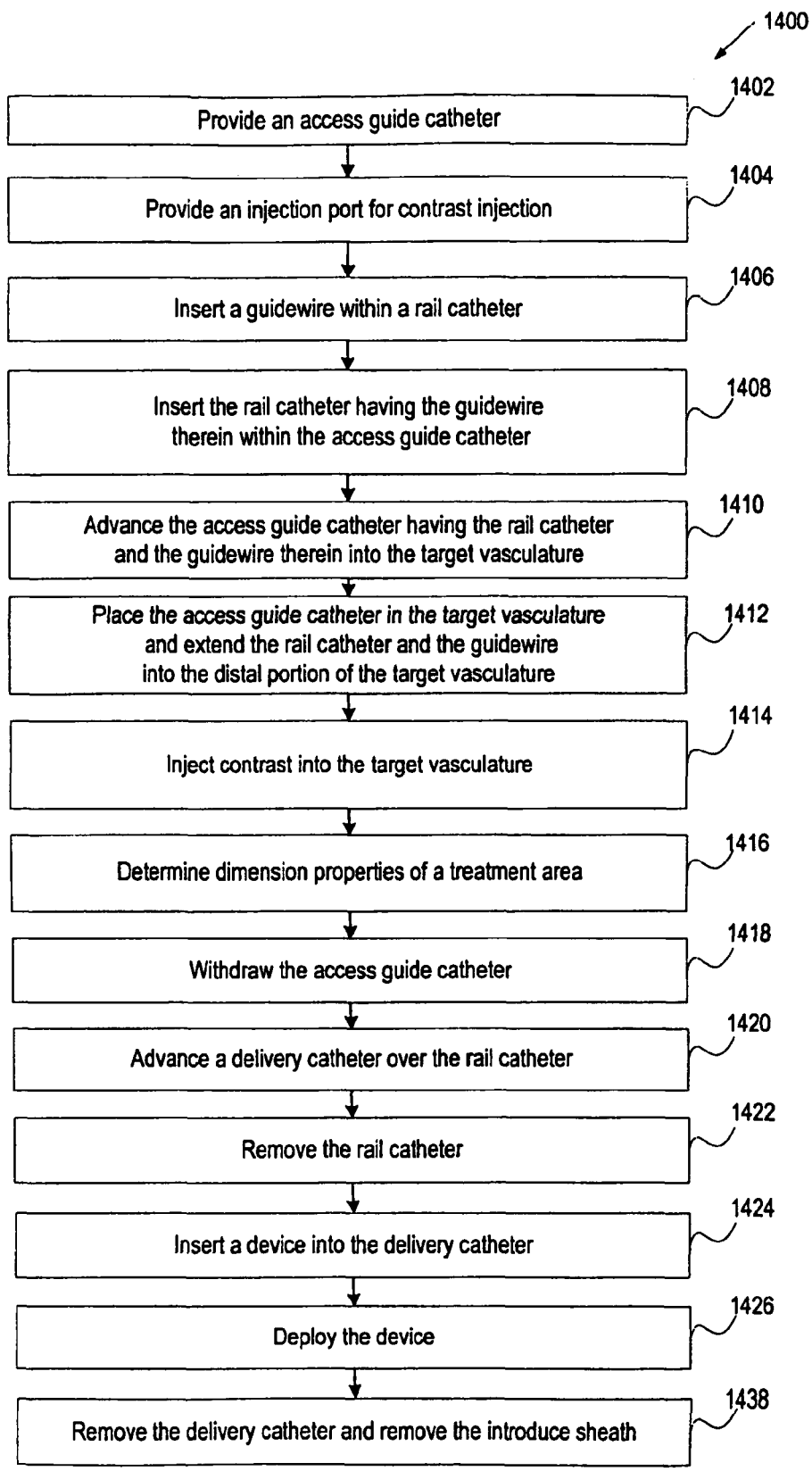
FIG. 14 illustrates another method of delivering a device into a target vasculature in accordance to embodiments of the present invention.

FIG. 14 illustrates another exemplary embodiment (method 1400) of delivering a device (e.g., a Mitral valve repair device) into a target vasculature (e.g., the coronary sinus and the great cardiac vein). At box 1402, an access guide catheter is provided. At box 1404, an injection port is provided for contrast injection as previously described. The contrast solution may be injected through the rail catheter or the access guide catheter as previously described. In some embodiments, the injection port is a part of a rotating hemostatic valve (RHV) or other like device with a sidearm (an access port for injections). In another embodiment, the sidearm access port may be incorporated into the proximal port (Luer) of the access guide catheter. If the injection port is used on the access guide catheter, the injection port is usually coupled to the access guide catheter before the rail catheter is inserted. At box 1406, a guidewire is inserted within a rail catheter and is retracted just proximal to the distal tip of the rail catheter. The guidewire can be locked, clamped or held in position relative to the rail catheter. The guidewire can be held in position relative to the rail catheter at its proximal end. At box 1408, the rail catheter having the guidewire disposed therein is inserted within the access guide catheter until the rail catheter is near the distal tip of the access guide catheter.

At box 1410, the access guide catheter having the rail catheter and the guidewire disposed therein is advanced into the target vasculature. In one embodiment, the access guide catheter together with the rail catheter is advanced through an introducer sheath that has been inserted into a peripheral vessel that can lead to the target vasculature. In another embodiment, the access guide catheter having the rail catheter and the guidewire disposed therein is placed in the target vasculature using other known techniques such as surgical procedures through the patient's chest. In these embodiments, the guidewire and/or the rail catheter may extend from the distal end of the access guide catheter to help straighten and guide the access guide catheter through the vasculature in an atraumatic manner. As before, in some embodiments, the use of the guidewire may be omitted and the rail catheter used exclusively to gain the distal access or, if the rail catheter fails to gain the desired distal access, the guidewire may then be inserted into the proximal end of the rail catheter and out its distal end to gain the desired distal access. In one embodiment, the target vasculature is a coronary sinus. At box 1412, the access guide catheter is manipulated to engage the target vasculature. The rail catheter and the guidewire are extending more distally from the access guide catheter to enter a more distal portion of the target vasculature. In one embodiment, the access guide catheter is manipulated to allow it to engage the ostium of the coronary sinus and the guidewire and the rail catheter extend distally from the coronary sinus ostium and into the great cardiac vein.

At box 1414, a contrast solution is injected into the target vasculature and its distal portion via the access guide catheter and/or the rail catheter to allow for fluoroscopic visualization of the anatomy of the target vasculature as well as visualization of the position of the access guide catheter and rail catheter assembly relative to that anatomy. The position of the rail catheter may then be adjusted to cross the desired treatment area based on the visualization of the vascular structure. As previously described, other catheters and/or other contrast injections may be used to determine the landmarks of the desired treatment anatomy by fluoroscopic visualization. At box 1416, the dimension properties such as length and/or diameter(s) of a treatment area are determined to allow for an appropriate size of a medical/diagnostic device and/or a delivery catheter to be selected. In one embodiment, the length of the distal portion of the delivery catheter is selected based on a fluoroscopic length measurement. Similar to previous embodiments, the rail catheter includes a plurality of radiopaque markers placed at known intervals and with the contrast injected, the anatomy and length of the treatment site in the target vasculature can be determined. The rail catheter or the guidewire can also include such markers for similar functions in length determination. Additionally, similar to current practice, the diameter(s) of the treatment area can be determined by comparing the known OD of the access guide catheter and/or the rail catheter to the width of the vessel during contrast injection and visualization.

At box 1418, the access guide catheter is withdrawn proximally out of the introducer sheath and off of the OD of the rail catheter. At box 1420, a delivery catheter is advanced distally over the rail catheter and through the introducer sheath. At box 1422, when the delivery catheter is in position, the rail catheter and the guidewire are removed. At box 1424, a therapeutic and/or diagnostic device is inserted into the delivery catheter. At box 1426, the device is deployed. In one embodiment, the device is deployed within the coronary sinus and/or the great cardiac vein. In one embodiment, to deploy the device, the delivery catheter is retracted proximally while the device is held in place to allow the device to be exposed and deployed into the vasculature. In some embodiments, exposing the device is all that is necessary to deploy the device in the target vasculature. In other embodiments, the device is incorporated in a device catheter (or a device's delivery system) and thus the device catheter plus the device are inserted through the delivery catheter. To deploy the device, the device catheter may need to be manipulated and then removed as previously discussed.

In one embodiment, the device is a Mitral valve repair system including a distal anchoring member and a proximal anchoring member connected by a telescoping assembly as previously disclosed. A cord is included in the Mitral valve repair system to lock the system in place. The Mitral valve repair system is typically housed in its own device catheter or delivery system. In the embodiment where the device is a Mitral valve repair system, the delivery catheter is withdrawn proximally in order to expose the Mitral valve repair system. A portion of the device catheter is then withdrawn proximally to expose and deploy the distal anchoring member. The distal anchoring member is deployed by expanding (e.g., self-expanding) such that it contacts the inner wall of the target vasculature. Once the distal anchoring member is deployed, the delivery catheter and the device catheter are withdrawn more proximally (e.g., to the ostium of the coronary sinus). The proximal anchoring member is then placed in a desired position. The proximal anchoring member is then deployed in a similar manner as described for the distal anchoring member, and in one embodiment, at the entrance of the coronary sinus. The telescoping member is then adjusted to provide the cinching of the Mitral valve annulus to reverse Mitral valve regurgitation. In one embodiment, the Mitral valve repair system includes a pull loop that can be used to pull on the cord (via another loop at the proximal end of the cord) to make the adjustment. The pull loop is broken and is withdrawn from contact with the cord (the loop at the proximal end of the cord) when the Mitral valve repair system is locked in place (when the distal anchoring member and the proximal anchoring member are locked in place). With the pull loop withdrawn, the device is freed from its delivery system and the device is fully deployed. The delivery system may then be withdrawn from the delivery catheter, leaving the deployed device in the vasculature. At box 1438, after the device is deployed, the delivery catheter and then introducer sheath are withdrawn completely.

While particular embodiments of the present invention have been shown and described, it will be obvious to those skilled in the art that changes and modifications can be made without departing from this invention in its broader aspects and, therefore, the appended claims are to encompass within their scope all such changes and modifications as fall within the scope of this invention.

We claim:

1. A kit comprising:
    an access guide catheter having a inside diameter (ID);
    a rail catheter slideably disposable within the access guide catheter, the rail catheter having a detachable access port positioned on a proximal end thereof and an outside diameter (OD) that is smaller than the access guide catheter ID such that upon removal of the detachable access port the access guide catheter is capable of being proximally withdrawn over and removed from the rail catheter;
    a delivery catheter slideably disposable over the rail catheter, the delivery catheter having an ID that is larger than the rail catheter OD such that upon removal of the access guide catheter the delivery catheter is capable of being initially advanced over the rail catheter; and
    a mitral valve repair device disposable within the delivery catheter;
    wherein the delivery catheter ID is about the same as the access guide catheter ID.

2. The kit of claim 1 wherein the rail catheter OD is about 0.002-0.010 inches smaller than the delivery catheter ID.

3. The kit of claim 2 wherein the rail catheter OD is about 0.002-0.010 inches smaller than the access guide catheter ID.

4. A kit for treating a mitral valve comprising:
    a coronary sinus access system, the coronary sinus access system including:
        an access guide catheter to sub-select a coronary sinus;
        a rail catheter, the rail catheter disposable into the access guide catheter and capable of extending distally from the access guide catheter into a distal portion of the coronary sinus, the rail catheter having a detachable access port positioned on a proximal end thereof and a central lumen extending through a distal body section and distal tip section thereof, the central lumen having a substantially restricted cross section at the distal tip section relative to the distal body section;
        a delivery catheter disposable over the rail catheter, wherein after the delivery catheter is disposed over the rail catheter, the rail catheter is configured to be removed from the coronary sinus; and
    a mitral valve repair device disposable within the delivery catheter and configured to be positioned at the treatment site after the rail catheter is removed from the coronary sinus;
    wherein the delivery catheter has an inside diameter (ID) that is about the same as an ID of the access guide catheter, and detachment of the access port from the rail catheter allows the access guide catheter to be removed from over the rail catheter, and for the delivery catheter to be initially advanced over the rail catheter to the coronary sinus after the access guide catheter is removed from over the rail catheter.

5. The kit of claim 4 wherein the mitral valve repair device includes a distal anchoring member, a proximal anchoring member, and a telescoping assembly, the telescoping assembly coupling at a first end to the distal anchoring member and coupling at a second end to the proximal anchoring member.

6. The kit of claim 4 wherein the rail catheter includes one or more markers, the markers providing measurements for the treatment site.

7. The kit of claim 4 wherein anyone or both of the access guide catheter and the rail catheter is configured to enable a contrast solution to be injected therethrough or over to enable visualization of the coronary sinus.

8. The kit of claim 4 wherein the rail catheter includes a guidewire lumen for a guidewire to be inserted therethrough.

9. The kit of claim 8 further comprising:
    a guidewire to be inserted through the guidewire lumen.

10. The kit of claim 9 wherein the guidewire further comprising:

one or more markers, the markers providing measurements for the treatment site.

11. The kit of claim 4 wherein the access guide catheter is configured to support the rail catheter.

12. The kit of claim 4 wherein anyone or both of the rail catheter and the delivery catheter includes a flexible and/or bent distal end portion.

13. The kit of claim 4 wherein the flexible and/or bent distal end portion is configured to conform to the shape the coronary sinus.

14. The kit of claim 4 wherein the rail catheter has a guidewire disposed therein.

15. The kit of claim 4 wherein the rail catheter has a guidewire locking portion to lock a guidewire in position relative to the rail catheter.

16. The kit of claim 4 wherein the rail catheter has an outside diameter (OD) that is about 0.002-0.010 inches smaller than the inside diameter (ID) of the delivery catheter.

17. The kit of claim 16 wherein the rail catheter has an outside diameter (OD) that is about 0.002-0.010 inches smaller than an inside diameter (ID) of the access guide catheter.

* * * * *